US012100515B2

(12) United States Patent
Humble et al.

(10) Patent No.: US 12,100,515 B2
(45) Date of Patent: Sep. 24, 2024

(54) ALTERING A TARGETED BRAIN THERAPEUTIC BASED ON A BRAIN CIRCUIT MODEL

(71) Applicant: International Business Machines Corporation, Armonk, NY (US)

(72) Inventors: James Humble, Putnam Valley, NY (US); James R. Kozloski, New Fairfield, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 958 days.

(21) Appl. No.: 16/508,869

(22) Filed: Jul. 11, 2019

(65) Prior Publication Data

US 2021/0012907 A1   Jan. 14, 2021

(51) Int. Cl.
| | | |
|---|---|---|
| G16H 50/50 | (2018.01) | |
| A61B 6/03 | (2006.01) | |
| G06N 3/008 | (2023.01) | |
| G06N 3/065 | (2023.01) | |
| G09B 23/28 | (2006.01) | |
| G16H 50/20 | (2018.01) | |

(52) U.S. Cl.
CPC ............ *G16H 50/50* (2018.01); *A61B 6/037* (2013.01); *G06N 3/008* (2013.01); *G06N 3/065* (2023.01); *G09B 23/28* (2013.01); *G16H 50/20* (2018.01)

(58) Field of Classification Search
CPC .......... A61B 6/037; G06N 3/00; G06N 3/008; G06N 3/0635; G09B 23/28
See application file for complete search history.

(56) References Cited

U.S. PATENT DOCUMENTS

| | | | |
|---|---|---|---|
| 6,647,358 B2 | 11/2003 | Grass | |
| 7,899,225 B2 | 3/2011 | Collins et al. | |
| 8,150,629 B2 | 4/2012 | Geerts | |
| 10,650,512 B2* | 5/2020 | Hoff | G06T 7/0012 |
| 2004/0009459 A1 | 1/2004 | Anderson | |
| 2004/0122703 A1 | 6/2004 | Walker | |
| 2005/0187461 A1* | 8/2005 | Murphy | G06K 9/00 600/416 |
| 2007/0106479 A1* | 5/2007 | Geerts | G16H 50/50 703/11 |
| 2008/0097197 A1 | 4/2008 | Kalafut | |

(Continued)

FOREIGN PATENT DOCUMENTS

EP    2028608 A2    2/2009

OTHER PUBLICATIONS

Santaniello et al., "Systems approaches to optimizing deep brain stimulation therapies in Parkinson's disease." WIREs Syst Biol Med. 10:e1421. (2018).

(Continued)

*Primary Examiner* — Timothy A Musselman
(74) *Attorney, Agent, or Firm* — Amin, Turocy & Watson, LLP

(57) ABSTRACT

Techniques that facilitate altering a targeted brain therapeutic are provided. In one example, a system determines parameter data associated with a circuit model of a biological brain. The system also simulates the circuit model based on the parameter data to generate treatment data associated with the biological brain.

20 Claims, 12 Drawing Sheets

(56) References Cited

U.S. PATENT DOCUMENTS

| | | | | |
|---|---|---|---|---|
| 2009/0114849 | A1* | 5/2009 | Schneider | A61N 5/1039 |
| | | | | 250/492.1 |
| 2009/0182697 | A1 | 7/2009 | Massaquoi | |
| 2009/0234626 | A1 | 9/2009 | Yu et al. | |
| 2014/0214730 | A9 | 7/2014 | Shahaf | |
| 2015/0206051 | A1 | 7/2015 | McIntosh | |
| 2016/0038463 | A1* | 2/2016 | Gallagher | A61K 31/19 |
| | | | | 435/7.1 |
| 2016/0171383 | A1* | 6/2016 | Narain | G16H 50/70 |
| | | | | 706/52 |
| 2017/0286629 | A1 | 10/2017 | Jannin | |
| 2018/0350066 | A1* | 12/2018 | Zuyev | G06T 7/0012 |

OTHER PUBLICATIONS

Mayberg, "Targeted electrode-based modulation of neural circuits for depression." J. Clin Invest. 119(4): 717-725. (2009).

Gunalan et al., "Creating and parameterizing patient-specific deep brain stimulation pathway-activation models using the hyperdirect pathway as an example." PLoS One 12(4): e0176132 (2017).

Joshi et al., "An integrated modelling framework for neural circuits with multiple neuromodulators, Journal of The Royal Society Interface." Journal of the Royal Society Interface, vol. 14, No. 126, 20160902, 2017, http://doi.org/10.1098/rsif. (2016).

Deco, "Great Expectations: Using Whole-Brain Computational Connectomics for Understanding Neuropsychiatric Disorders." vol. 84, issue 5, pp. 892-905. Dec. 3, 2014.

News Update. "Alzheimer's Disease Treatment Market to Exceed $13 Billion by 2023, says Report" PharmExec.com May (2015).

Valldeoriola. "Cost and Efficacy of Therapies for Advanced Parkinson's Disease" IntechOpen DOI: 10.5772/17862 (Nov. 2011).

Bushak. "The Stress Of Severe Pain: 11% Of Americans Suffer From Chronic Pain, NIH States" Medical Daily, The Grapevine (Aug. 2015).

Bhisey. "Pain Management Therapeutics Market to Reach US$83.0 Billion by 2024; Transparency Market Research" Transparency market Research (Sep. 2016).

Koskie. "Depression: Facts, Statistics, and You" healthline (Jun. 2018).

"Parkinson's disease" from Wikipedia web accessed on Apr. 26, 2019 at: https://en.wikipedia.org/wiki/Parkinson%27s_disease.

"The Global Huntington's Disease Therapeutics Market Trends, Drivers & Projections" Gobal Industry Analystis, Inc. web accessed: https://www.strategyr.com/MarketResearch/Huntingtons_Disease_Therapeutics_Market_Trends.asp (Mar. 2015).

"2017 Alzheimer's Statistics" alzheimers.net web accessed: https://www.alzheimers.net/resources/alzheimers-statistics/.

Kessler. "The Costs of Depression" National Institutes of Health NIH-PA Athor Manuscript. (2013).

Pune. "Personalized Medicine Market Worth $149+ Billion by 2020 Covering Companion Diagnostic and Targeted Therapeutics" Marketwatch (Feb. 2016).

Dorszewska. "Serotonin in Neurological Diseases" Intech (2017).

"Norepinephrine transporter" from Wikipedia web accessed on Apr. 26, 2019 at: https://en.wikipedia.org/wiki/Norepinephrine_transporter#Clinical_significance.

Maramai. "Dopamine D3 Receptor Antagonists as Potential Therapeutics for the Treatment of Neurological Diseases" frontiers in Neuroscience/ Neuropharmacology (Oct. 2016).

"Florbetapir (18F)" from Wikipedia web accessed on Apr. 26, 2019 at: https://en.wikipedia.org/wiki/Florbetapir_(18F).

Flumazenil from Wikipedia web accessed on Apr. 26, 2019 at: https://en.wikipedia.org/wiki/Flumazenil.

Mefway (18F) from Wikipedia web accessed on Apr. 26, 2019 at: https://en.wikipedia.org/wiki/Mefway_(18F).

"MPPF" from Wikipedia web accessed on Apr. 26, 2019 at: https://en.wikipedia.org/wiki/MPPF.

"Pittsburgh compound B" from Wikipedia web accessed on Apr. 26, 2019 at: https://en.wikipedia.org/wiki/Pittsburgh_compound_B.

Sadigh-Eteghad, et al., "Regulation of nicotinic acetylcholine receptors in Alzheimer's disease: apossible role of chaperones," http://dx.doi.org/10.1016/j.ejphar.2015.02.047, 31 pages.

* cited by examiner

ALTERING A TARGETED BRAIN THERAPEUTIC BASED ON A BRAIN CIRCUIT MODEL

BACKGROUND

The subject disclosure relates generally to medical systems, and more specifically, to managing medical therapeutics using artificial intelligence.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate altering a targeted brain therapeutic based on a brain circuit model are described.

According to an embodiment, a system can comprise a circuit model configuration component and a circuit model simulation component. The circuit model configuration component can determine parameter data associated with a circuit model of a biological brain. The circuit model simulation component can simulate the circuit model based on the parameter data to generate treatment data associated with the biological brain.

According to another embodiment, a computer-implemented method is provided. The computer-implemented method can comprise determining, by a system operatively coupled to a processor, parameter data associated with a circuit model that simulates behavior of a biological brain based on receptor pattern data indicative of receptor expression levels associated with medical imaging data. The computer-implemented method can also comprise parameterizing, by the system, the circuit model based on circuit data indicative of information for circuit properties associated with one or more medical conditions. Furthermore, the computer-implemented method can comprise simulating, by the system, the circuit model based on the parameter data to generate treatment data indicative of information for a treatment type and a treatment location associated with the biological brain.

According to yet another embodiment, a computer program product for product facilitating altering a targeted brain therapeutic can comprise a computer readable storage medium having program instructions embodied therewith. The program instructions can be executable by a processor and cause the processor to determine, by the processor, parameter data associated with a circuit model that simulates behavior of a biological brain based on receptor pattern data indicative of receptor expression levels associated with medical imaging data. The program instructions can also cause the processor to simulate, by the processor, the circuit model based on the parameter data to generate treatment data indicative of information for a treatment type and a treatment location associated with the biological brain.

DETAILED DESCRIPTION

Figure 1:
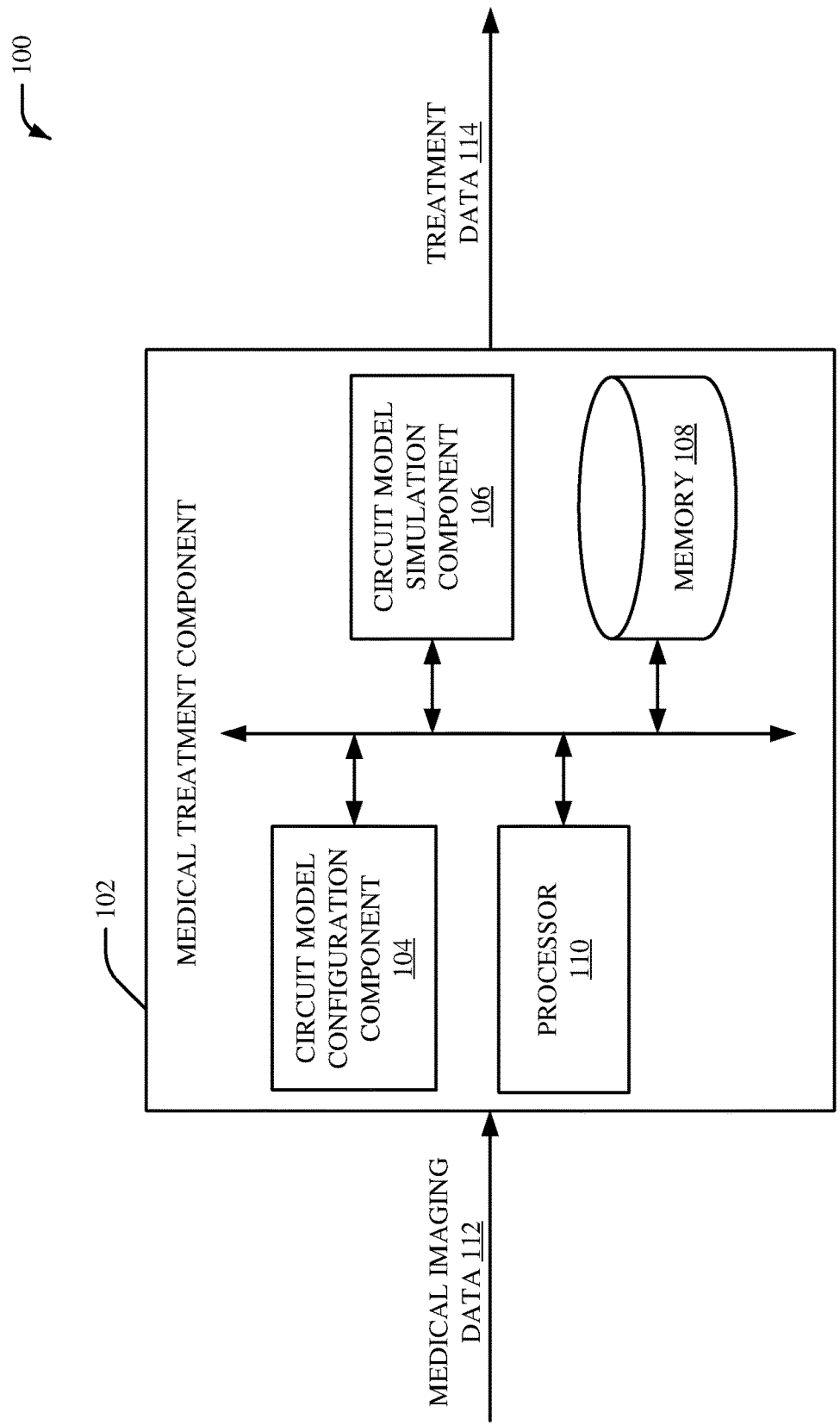
FIG. 1 illustrates a block diagram of an example, non-limiting system that includes a medical treatment component in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Medical imaging systems such as positron emission tomography (PET) systems employ radiotracers to label and/or quantify aspects of receptors in a brain to, for example, facilitate diagnosis and/or monitoring of medical conditions associated with the brain. Pharmaceutical therapy injections and/or gene therapy injections can be employed, for example, to treat medical conditions associated with a brain. However, pharmaceutical therapy injections and/or gene therapy injections can have different effects if targeted at different locations in a brain. As such, determining a correct location for pharmaceutical therapy injections and/or gene therapy injections is generally important for effective treatment of a medical condition. A medical condition can include, for example, a neurological medical condition such as Huntington's disease, Alzheimer's disease, Parkinson's disease, dystonia, chronic pain, depression, stroke, a motor neuron condition, certain forms of cancer, etc. In an example, deep brain stimulation (DBS) can provide a treatment for medical conditions associated with the brain by implanting electrodes within areas of the brain related to the receptors in the brain. In another example, transcranial magnetic stimulation (TMS) can provide a treatment for medical conditions associated with the brain by employing magnetic fields for areas of the brain related to the receptors in the brain. Accordingly, efficacy of DBS and TMS is dependent on a location in brain. Furthermore, determining an optimal location for DBS and/or TMS is generally important for effective treatment of a medical condition using DBS and/or TMS. However, determining a correct location for a pharmaceutical therapy injection and/or a gene therapy injection (e.g., determining a correct location for DBS and/or TMS) is generally limited to trial-and-error. Furthermore, it is generally difficult to personalize a treatment for a medical condition using conventional techniques for pharmaceutical therapy injection and/or a gene therapy injection (e.g., conventional techniques for DBS and/or TMS).

To address these and/or other issues, embodiments described herein include systems, computer-implemented methods, and computer program products for altering a targeted brain therapeutic based on a brain circuit model. For instance, targeting of a brain therapeutic can be altered based on a continuous neural circuit model. A brain therapeutic can be associated with a pharmaceutical therapy injection and/or a gene therapy injection. For example, a brain therapeutic can be realized via DBS and/or TMS. In an aspect, PET data can be employed to provide a constrained brain circuit model. For example, PET data can be employed to establish receptor expression level targets for a brain circuit model. The brain circuit model can be a feedback model of synaptic efficacy corresponding to an anatomical brain. In an embodiment, one or more circuit parameters, synaptic efficacy and/or one or more internal model states can estimated from the PET data. Furthermore, based on the one or more brain circuit parameters, the synaptic efficacy and/or the one or more internal model states, one or more direct constraints can be realized on a brain circuit model. The brain circuit model can be perturbed at one or more locations with respect to a brain in order to predict therapeutic effects based on the one or more brain circuit parameters, the synaptic efficacy and/or the one or more internal model states. In certain embodiments, a ranking of therapeutic effects can be provided to allow a determination of an optimal location for therapeutic inputs by a pharmaceutical therapy injection and/or a gene therapy injection. Additionally or alternatively, in certain embodiments, a ranking of therapeutic effects can be provided to allow a determination of an optimal type of therapeutic such as, for example, a specific pharmaceutical therapy injection type, a specific gene therapy injection type, DBS, or TMS.

In an embodiment, a method for ranking therapeutic approaches for therapeutic intervention can be provided, where the therapeutic approaches include at least one of a set of possible brain regions, a set of possible medication doses, and/or a set of brain stimulation parameters. The method can include receiving a set of PET voxel measures of brain expression levels, calculating receptor expression levels from the PET voxel data, parameterizing a set of expression level models to match the voxel measures, simulating the internal model of circuit feedback given the expression level model and additional cell/internal model properties relevant to disease, transferring parameters found for the expression level to a voxel model and/or to a disease model of circuit dysfunction for parameterization of a circuit simulation, simulating forward the circuit model and producing a predicted patient specific baseline trajectory. In certain embodiments, one or more portions of the method can be repeated for multiple patient PET scans. Additionally or alternatively, the method can include applying numerous perturbations based on therapeutics approaches to the circuit model and simulating forward the circuit model and producing predicted patient specific perturbed trajectories, ranking the outcomes of the perturbations based on a measure of resolution of circuit dysfunction relevant to disease, and/or using the ranked perturbations and patient specific baseline/perturbed trajectories for prognostic enrichment in clinical trials (e.g., for patient cohort segregation and selection).

In an embodiment, a system for ranking therapeutic approaches for therapeutic intervention can be provided, where the therapeutic approaches include at least one of a set of possible brain regions, a set of possible medication doses, and/or a set of brain stimulation parameters. The system can include a PET analyzer, a PET voxel modeler, a circuit model optimizer, a patient model optimizer, a circuit modeler, a therapeutic design component, and/or a prognostic enrichment component. The PET analyzer can calculate receptor expression levels from patient PET data. The PET voxel modeler can simulate an internal model of circuit feedback given output from the PET analyzer and/or additional cell/internal model properties relevant to a disease. The circuit model optimizer can parameterize a circuit simulation given circuit properties relevant to a disease. The patient model optimizer can parameterize a circuit simulation given patient specific circuit parameters from the PET voxel modeler. The circuit modeler can simulate the circuit forward and/or can produce a predicted patient specific baseline trajectory. The therapeutic design component can apply targeted therapeutics from numerous perturbations to a circuit model. The therapeutic design component can additionally or alternatively simulate forward and/or can produce predicted patient specific perturbed trajectories. The prognostic enrichment component can segregate and/or select patient cohorts given patient specific ranked therapeutics and/or predicted patient specific perturbed trajectories provided by the therapeutic design component.

As such, an optimal treatment type and/or an optimal location for a treatment associated with a medical condition can be determined. Furthermore, an improved circuit model (e.g., an improved brain circuit model) can be provided to facilitate determination of an optimal treatment type and/or an optimal location for a treatment associated with a medical condition. Moreover, a personalized treatment for a medical condition can be provided to a patient. Prognostic enrichment for a medical condition can also be provided by allowing direct testing of therapeutics and/or interventions for the medical condition via modeling of different perturbations of treatment type and/or treatment location.

FIG. 1 illustrates a block diagram of an example, non-limiting system 100 that facilitates altering a targeted brain therapeutic based on a brain circuit model in accordance with one or more embodiments described herein. In various embodiments, the system 100 can be a medical system associated with technologies such as, but not limited to, medical device technologies, medical imaging technologies, computational neuroscience technologies, brain modeling technologies, pharmaceutical therapy injection technologies, gene therapy injection technologies, DBS technologies, TMS technologies, PET scan technologies, healthcare technologies, computing technologies, data analytics technologies, modeling technologies, simulation technologies, machine learning technologies, artificial intelligence technologies, digital technologies, data analysis technologies, cloud computing technologies, computer technologies, server technologies, and/or other technologies. The system 100 can employ hardware and/or software to solve problems that are highly technical in nature, that are not abstract and that cannot be performed as a set of mental acts by a human. Further, some of the processes performed may be performed by one or more specialized computers (e.g., one or more specialized processing units, a specialized computer with a medical treatment component, etc.) for carrying out defined tasks related to altering a targeted brain therapeutic based on a brain circuit model. The system 100 and/or components of the system can be employed to solve new problems that arise through advancements in technologies mentioned above and/or computer architecture, and the like. One or more embodiments of the system 100 can provide technical improvements to a system associated with technologies such as, but not limited to, medical systems, medical device systems, medical imaging systems, computational neuroscience systems, brain modeling systems, pharmaceutical therapy injection systems, gene therapy injection systems, DBS systems, TMS systems, PET scan systems, healthcare systems, computing systems, data analytics systems, modeling systems, simulation systems, machine learning systems, artificial intelligence systems, digital systems, data analysis systems, cloud computing systems, computer systems, server systems, and/or other systems.

In the embodiment shown in FIG. 1, the system 100 can include a medical treatment component 102. As shown in FIG. 1, the medical treatment component 102 can include a circuit model configuration component 104 and a circuit model simulation component 106. Aspects of the medical treatment component 102 can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. In an aspect, the medical treatment component 102 can also include memory 108 that stores computer executable components and instructions. Furthermore, the medical treatment component 102 can include a processor 110 to facilitate execution of the instructions (e.g., computer executable components and corresponding instructions) by the medical treatment component 102. As shown, the circuit model configuration component 104, the circuit model simulation component 106, the memory 108 and/or the processor 110 can be electrically and/or communicatively coupled to one another in one or more embodiments. In certain embodiments, the medical treatment component 102 can be in communication with a wearable device system and/or a cloud computing system.

The medical treatment component 102 (e.g., the circuit model configuration component 104 of the medical treatment component 102) can receive medical imaging data 112. The medical imaging data 112 can be medical imagery associated with image pixel data. For example, the medical imaging data 112 can be medical imagery where respective radioactivity concentration values are assigned to respective image pixels. The medical imaging data 112 can be generated by one or more medical imaging devices associated with a set of sensors. A medical imaging device from the one or more medical imaging devices can be a PET device, a computed tomography (CT) device, a magnetic resonance imaging (MRI) device, a computed axial tomography (CAT) device, an ultrasound device, or another type of medical imaging device. The medical imaging data 112 two-dimensional (2D) medical imaging data and/or three-dimensional (3D) medical imaging data. In certain embodiments, the medical imaging data 112 can be multi-dimensional medical imaging data (e.g., 3D medical imaging data) associated with one or more medical imaging devices. For instance, the medical imaging data 112 can be a set medical images and/or a set of data captured via two or more medical imaging devices. In an example, the medical imaging data 112 can be a set medical images and/or a set of data captured via a PET device, a CT device and/or an MRI device. The medical imaging data 112 can be received directly from one or more medical imaging devices. Alternatively, the medical imaging data 112 can be stored in one or more databases that receives and/or stores the medical imaging data associated with the one or more medical imaging devices.

In an embodiment, the circuit model configuration component 104 can determine parameter data associated with a circuit model (e.g., a brain circuit model) that simulates behavior of a biological brain. For instance, the circuit model configuration component 104 can determine parameter data associated with the circuit model based on the receptor pattern data associated with the medical imaging data 112. In an aspect, the circuit model can simulate transmission of signals between brain areas, neurons and/or receptors of a biological brain associated with a patient identity. In certain embodiments, the circuit model configuration component 104 can determine parameter data associated with the circuit model based on cannabinoid receptor expression levels associated with the medical imaging data 112, norepinephrine transporter expression levels associated with the medical imaging data 112, dopamine receptor expression levels associated with the medical imaging data 112, inhibitory receptor expression levels associated with the medical imaging data 112, nicotinic receptor expression levels associated with the medical imaging data 112, beta-amyloid plaque expression levels associated with the medical imaging data 112, and/or a different type of expression level associated with the medical imaging data 112. In an aspect, the circuit model configuration component 104 can determine receptor pattern data associated with the medical imaging data 112. Furthermore, the circuit model configuration component 104 can determine the parameter data based on the receptor pattern data. The receptor pattern data can be indicative of receptor expression levels associated with the medical imaging data 112. For instance, the circuit model configuration component 104 can measure respective receptor expression levels for respective voxels of the medical imaging data 112. In an example, the circuit model configuration component 104 can measure respective receptor expression levels for respective voxels of PET imaging data associated with the medical imaging data 112. A voxel can be an array of data elements of volume for a 3D space associated with the medical imaging data 112. In a non-limiting example, the receptor expression level can be cannabinoid receptor expression levels indicative of expression levels for cannabinoid receptors of a biological brain. Additionally or alternatively, the receptor expression level can be norepinephrine transporter expression levels indicative of expression levels for norepinephrine transporters of a biological brain. Additionally or alternatively, the receptor expression level can be dopamine receptor expression levels indicative of expression levels for dopamine receptors of a biological brain. Additionally or alternatively, the receptor expression level can be inhibitory receptor expression levels indicative of expression levels for inhibitory receptors of a biological brain. Additionally or alternatively, the nicotinic receptor level can be inhibitory receptor expression levels indicative of expression levels for nicotinic receptors of a biological brain. Additionally or alternatively, the nicotinic receptor level can be beta-amyloid plaque expression levels indicative of expression levels for beta-amyloid plaques of a biological brain. An expression level can be a level of production and/or availability of a biochemical indicator represented by a value of a voxel associated with the medical imaging data 112.

The circuit model simulation component 106 can simulate the circuit model based on the parameter data to generate treatment data 114 for the biological brain associated with the circuit model. The treatment data 114 can be indicative of information for a treatment type associated with the biological brain. For example, the treatment data 114 can include information for one or more types of treatments (e.g., one or more types of interventions) to perform with respect to the biological brain associated with the circuit model. A treatment type can include, for example, a specific pharmaceutical therapy injection type, a specific gene therapy injection type, DBS, TMS, and/or another type of treatment. Additionally or alternatively, the treatment data 114 can be indicative of a treatment location associated with the biological brain. For instance, the treatment data 114 can additionally or alternatively include information for one or more locations for performing the one or more types of treatments with respect to the biological brain associated with the circuit mode. In an example, the treatment data 114 can include one or more locations with respect to the biological brain to perform a pharmaceutical therapy injection treatment, one or more locations with respect to the biological brain to perform a gene therapy injection treatment, one or more locations with respect to the biological brain to perform a DBS treatment, one or more locations with respect to the biological brain to perform a TMS treatment, and/or one or more locations with respect to the biological brain to perform another type of treatment. A location with respect to the biological brain can be, for example, a brain region for a treatment. In certain embodiments, the treatment data 114 can include a ranking of treatment types associated with the biological brain. For example, treatment types associated with the biological brain can be ranked based on therapeutic effect with respect to the biological brain. In certain embodiments, the circuit model simulation component 106 can repeat simulation of the circuit model based on availability of additional medical imaging data. For example, the circuit model simulation component 106 can repeat simulation of the circuit model for different PET scans. Additionally or alternatively, the circuit model simulation component 106 can repeat simulation of the circuit model for respective perturbations of input parameter data for the circuit model. In certain embodiments, the circuit model simulation component 106 can rank a set of treatments associated with the treatment data 114. For example, the circuit model simulation component 106 can rank a set of treatments associated with the treatment data 114 based on optimal treatment type and/or optimal treatment location.

In certain embodiments, the circuit model simulation component 106 can employ machine learning and/or principles of artificial intelligence (e.g., a machine learning process) to simulate the circuit model based on the parameter data and/or the receptor pattern data. For example, the circuit model simulation component 106 can employ machine learning and/or principles of artificial intelligence (e.g., a machine learning process) to learn one or more patterns, one or more inferences, one or more correlations, one or more features and/or information related to the parameter data and/or the receptor pattern data. In an aspect, the circuit model simulation component 106 can employ machine learning and/or principles of artificial intelligence (e.g., a machine learning process) to generate the treatment data 114. The circuit model simulation component 106 can perform learning explicitly or implicitly with respect to learning one or more patterns, one or more inferences, one or more correlations, one or more features and/or information related to the parameter data and/or the receptor pattern data. In an aspect, the circuit model simulation component 106 can learn one or more patterns, one or more inferences, one or more correlations, one or more features and/or information related to the parameter data and/or the receptor pattern data based on classifications, correlations, inferences and/or expressions associated with principles of artificial intelligence. For instance, the circuit model simulation component 106 can employ an automatic classification system and/or an automatic classification process to learn one or more patterns, one or more inferences, one or more correlations, one or more features and/or information related to the parameter data and/or the receptor pattern data. In one example, the circuit model simulation component 106 can employ a probabilistic and/or statistical-based analysis (e.g., factoring into the analysis utilities and costs) to learn and/or generate inferences with respect to the parameter data and/or the receptor pattern data. In an aspect, the circuit model simulation component 106 can include an inference component (not shown) that can further enhance automated aspects of the circuit model simulation component 106 utilizing in part inference-based schemes to learn one or more patterns, one or more inferences, one or more correlations, one or more features and/or information related to the parameter data and/or the receptor pattern data.

The circuit model simulation component 106 can employ any suitable machine-learning based techniques, statistical-based techniques and/or probabilistic-based techniques. For example, the circuit model simulation component 106 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the circuit model simulation component 106 can perform a set of machine learning computations associated with learning one or more patterns, one or more inferences, one or more correlations, one or more features and/or information related to the parameter data and/or the receptor pattern data. For example, the circuit model simulation component 106 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations to learn one or more patterns, one or more inferences, one or more correlations, one or more features and/or information related to the parameter data and/or the receptor pattern data.

It is to be appreciated that the medical treatment component 102 (e.g., the circuit model configuration component 104 and/or the circuit model simulation component 106) performs a simulation process that cannot be performed by a human (e.g., is greater than the capability of a single human mind). For example, an amount of data processed, a speed of processing of data (e.g., a speed of processing data associated with multiple parties) and/or data types processed by the medical treatment component 102 (e.g., the circuit model configuration component 104 and/or the circuit model simulation component 106) over a certain period of time can be greater, faster and different than an amount, speed and data type that can be processed by a single human mind over the same period of time. The medical treatment component 102 (e.g., the circuit model configuration component 104 and/or the circuit model simulation component 106) can also be fully operational towards performing one or more other functions (e.g., fully powered on, fully executed, etc.) while also performing the above-referenced condition sensor analytics process. Moreover, the medical treatment component 102 (e.g., the circuit model configuration component 104 and/or the circuit model simulation component 106) can determine information that is impossible to obtain manually by a user. For example, a type of information included in the treatment data 114, an amount of information included in the treatment data 114 and/or a variety of information included in the treatment data 114 can be more complex than information obtained manually by a user.

Figure 2:
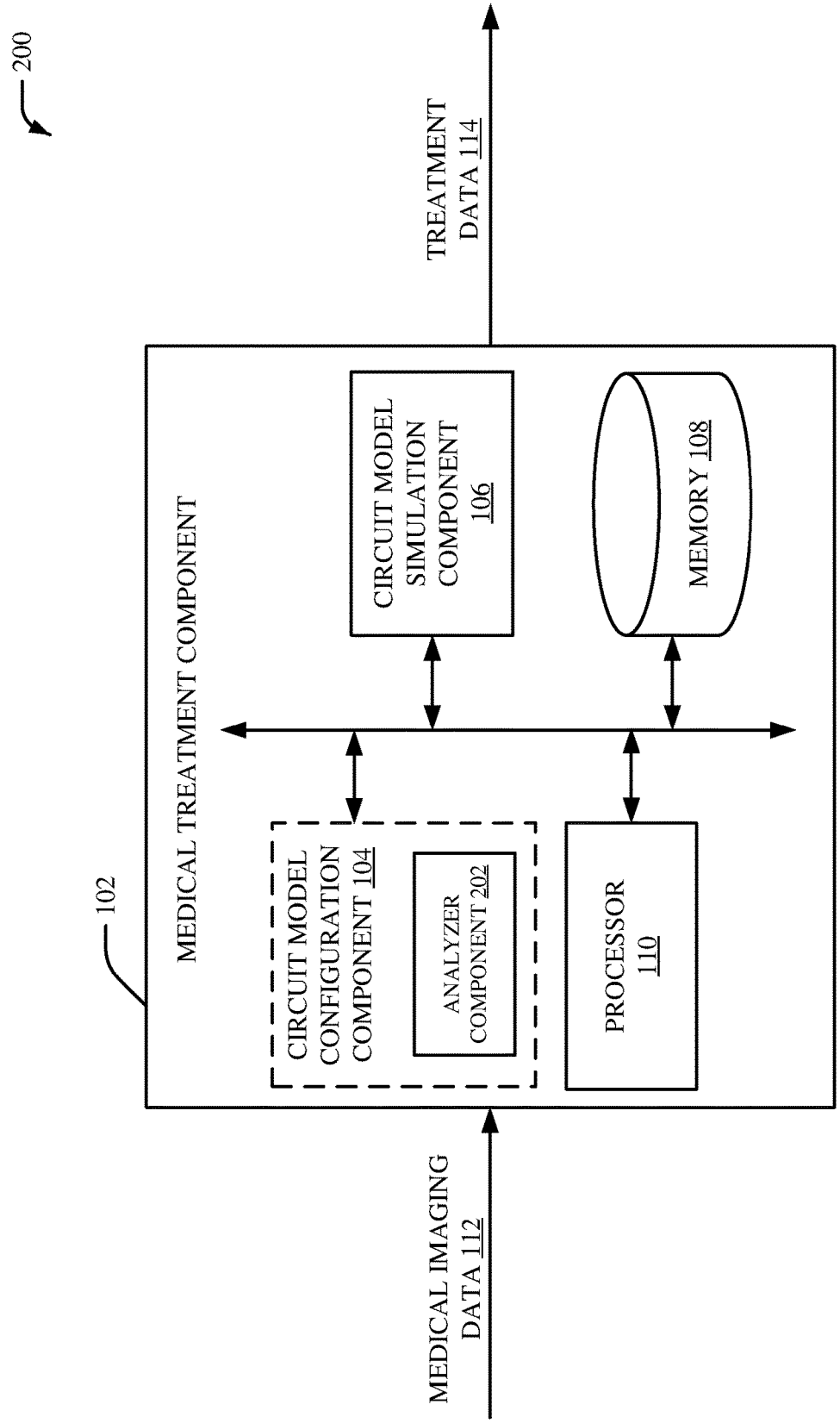
FIG. 2 illustrates a block diagram of another example, non-limiting system that includes a medical treatment component in accordance with one or more embodiments described herein.

FIG. 2 illustrates a block diagram of an example, non-limiting system 200 in accordance with one or more embodiments described herein. Repetitive description of like elements employed in other embodiments described herein is omitted for sake of brevity.

The system 200 includes the medical treatment component 102. The medical treatment component 102 can include the circuit model configuration component 104, the circuit model simulation component 106, the memory 108 and/or the processor 110. In the embodiment shown in FIG. 2, the circuit model configuration component 104 can include an analyzer component 202. The analyzer component 202 can analyze the medical imaging data 112. For instance, the analyzer component 202 can analyze image pixel data of the medical imaging data 112. In an example, the analyzer component 202 can determine radioactivity concentration values for respective image pixels of one or more medical images associated with the medical imaging data 112. In an embodiment, the analyzer component 202 can analyze image pixel data of PET imagery data associated with one or more PET devices. In certain embodiments, the analyzer component 202 can analyze 3D medical imaging data associated with the medical imaging data 112. For example, the analyzer component 202 can analyze one or more voxels associated with the medical imaging data 112. In an embodiment, the analyzer component 202 can determine receptor pattern data associated with the medical imaging data 112. For instance, the analyzer component 202 can determine receptor expression levels associated with the medical imaging data 112. In an aspect, the analyzer component 202 can calculate the receptor pattern data based on analysis of image pixel data for a set of medical images associated with the medical imaging data 112. In certain embodiments, the analyzer component 202 can analyze PET imagery data to calculate the receptor pattern data. For example, the analyzer component 202 can analyze PET imagery data to determine receptor expression levels associated with the medical imaging data 112. In certain embodiments, the analyzer component 202 can determine receptor pattern data based on a first portion of the medical imaging data 112 associated with a patient identity and second portion of the medical imaging data 112 associated with historical medical imaging data. For example, first portion of the medical imaging data 112 associated with a patient identity can be a PET imagery scan of a biological brain associated with the a patient identity. Furthermore, the second portion of the medical imaging data 112 associated with historical medical imaging data can include one or more PET imagery scans associated with a normal biological brain and/or one or more PET imagery scans associated with a biological brain related to a medical condition. A medical condition associated with a biological brain can include, for example, a neurological medical condition such as Huntington's disease, Alzheimer's disease, Parkinson's disease, dystonia, chronic pain, depression, stroke, a motor neuron condition, certain forms of cancer, etc. In certain embodiments, the analyzer component 202 can additionally determine receptor pattern data based on simulation data associated with a simulation of a circuit model. For example, simulation data employed by the analyzer component 202 can include data associated with a parameterization of a circuit model, data associated with one or more parameters of a circuit model, data associated with a predicted baseline trajectory associated with a circuit model, data associated with receptor expression level thresholds, and/or other data associated with a simulation of a circuit model.

Figure 3:
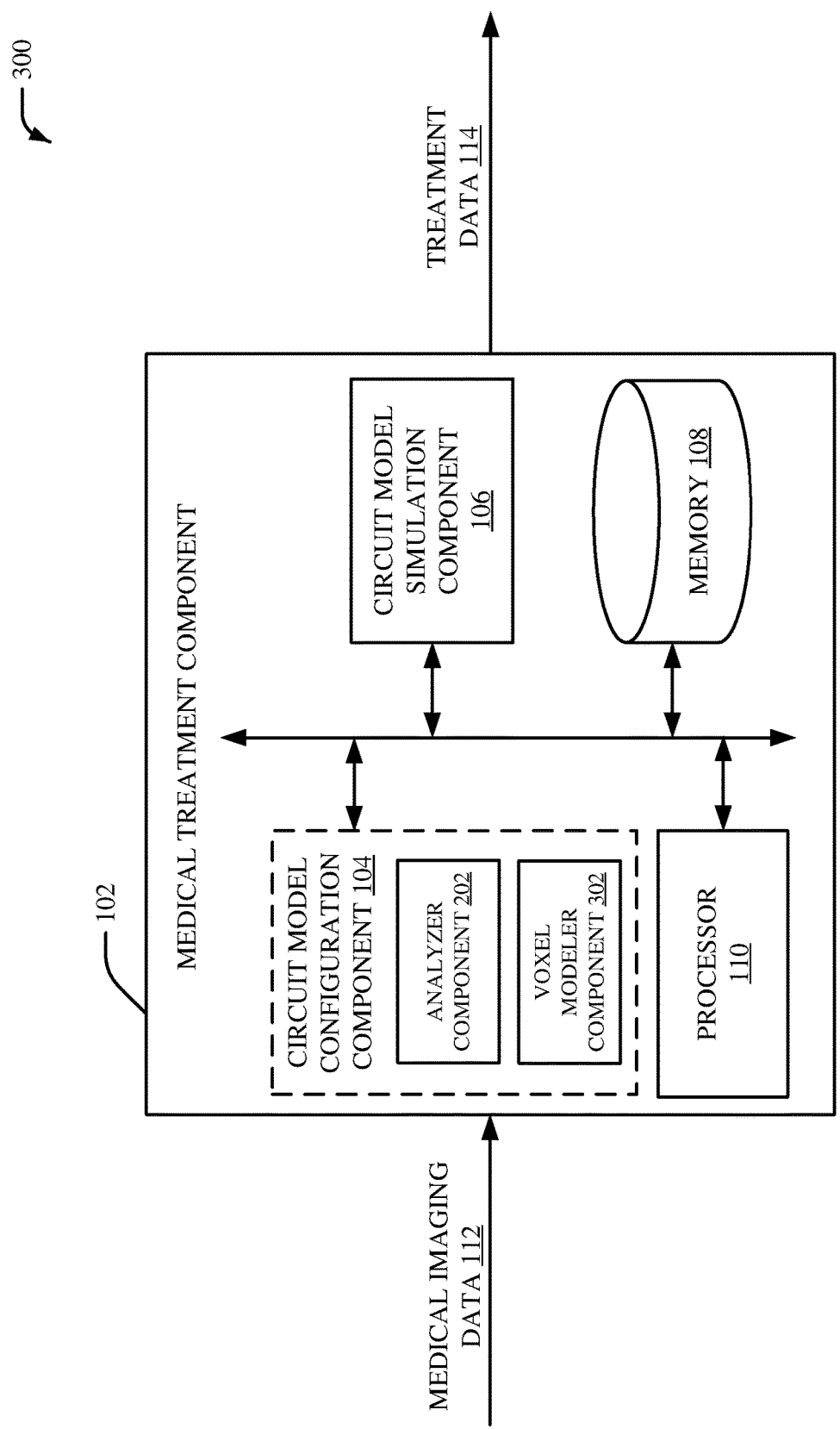
FIG. 3 illustrates a block diagram of yet another example, non-limiting system that includes a medical treatment component in accordance with one or more embodiments described herein.

FIG. 3 illustrates a block diagram of an example, non-limiting system 300 in accordance with one or more embodiments described herein. Repetitive description of like elements employed in other embodiments described herein is omitted for sake of brevity.

The system 300 includes the medical treatment component 102. The medical treatment component 102 can include the circuit model configuration component 104, the circuit model simulation component 106, the memory 108 and/or the processor 110. In the embodiment shown in FIG. 3, the circuit model configuration component 104 can include the analyzer component 202 and/or a voxel modeler component 302. The voxel modeler component 302 can simulate a set of voxel segments of the medical imaging data 112 to generate the parameter data. For instance, the voxel modeler component 302 can simulate a set of voxel segments for a circuit model of a biological brain. In an embodiment, the voxel modeler component 302 can simulate the set of voxel segments based on the receptor pattern data. For example, the voxel modeler component 302 can simulate receptor expression levels measured with a PET and included in voxels of the medical imaging data 112. Additionally or alternatively, the voxel modeler component 302 can simulate the set of voxel segments based on medical condition data indicative of information for properties associated with one or more medical conditions. The medical condition data can be related to one or more internal model properties of a circuit model. The one or more internal model properties can also be directly relevant to one or more medical conditions. For instance, the one or more internal model properties can be one or more cell properties related to one or more medical conditions. In an example, the one or more internal model properties can be one or more cell properties related to a first medical condition, one or more other cell properties related to a second medical condition, etc. The one or more internal model properties (e.g., the one or more cell properties) can include data associated with intrinsic cell excitability, data associated with cell channel properties, data associated with cell type, etc. In certain embodiments, the medical condition data can be generated based on a portion of the medical imaging data 112. For instance, the medical condition data can be generated based on one or more PET imagery scans associated with a normal biological brain and/or one or more PET imagery scans associated with a biological brain related to a medical condition. In an aspect, the voxel modeler component 302 can analyze a portion of the medical imaging data 112 (e.g., one or more PET imagery scans associated with a normal biological brain and/or one or more PET imagery scans associated with a biological brain related to a medical condition) to generate measurement thresholds associated with the medical condition data. In certain embodiments, the medical condition data can be obtained from one or more databases that store historical medical imaging data and/or historical measurement thresholds associated with one or more medical conditions. In certain embodiments, the voxel modeler component 302 can simulate the set of voxel segments based on medical condition data indicative of information for properties associated with a normal range for a medical condition. In an embodiment, the voxel modeler component 302 can simulate an internal model of the circuit model. For example, the voxel modeler component 302 can simulate an internal model of feedback of the circuit model. In an aspect, the voxel modeler component 302 can simulate one or more signal transmissions between voxels of the circuit model. For example, the voxel modeler component 302 can simulate excitatory neurotransmission between voxels of the circuit model. Additionally or alternatively, the voxel modeler component 302 can simulate inhibitory neurotransmission between voxels of the circuit model. In another aspect, control of receptor expression levels can be simulated based on constraints of measured receptor expression levels.

Figure 4:
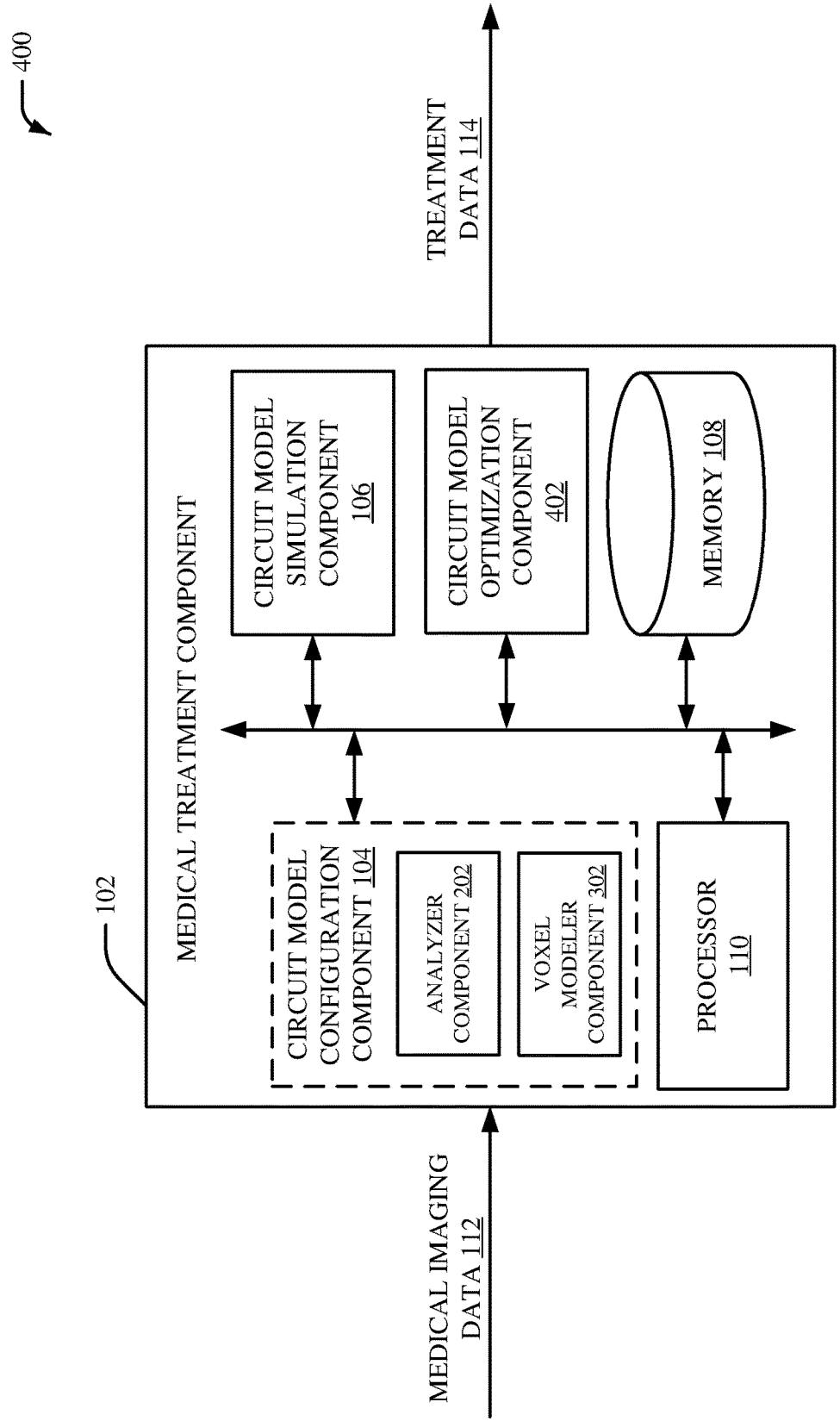
FIG. 4 illustrates a block diagram of yet another example, non-limiting system that includes a medical treatment component in accordance with one or more embodiments described herein.

FIG. 4 illustrates a block diagram of an example, non-limiting system 400 in accordance with one or more embodiments described herein. Repetitive description of like elements employed in other embodiments described herein is omitted for sake of brevity.

The system 400 includes the medical treatment component 102. The medical treatment component 102 can include the circuit model configuration component 104, the circuit model simulation component 106, a circuit model optimization component 402, the memory 108 and/or the processor 110. In the embodiment shown in FIG. 4, the circuit model configuration component 104 can include the analyzer component 202 and/or the voxel modeler component 302. The circuit model optimization component 402 can be employed to optimize the circuit model. For example, the circuit model optimization component 402 can be employed to optimize the circuit model based on circuit data. The circuit data can be indicative of information for circuit properties associated with one or more medical conditions. For example, the circuit data can be indicative of information for circuit properties for the circuit model for respective medical conditions. Additionally or alternatively, the circuit data can be indicative of information for circuit parameters associated with simulation of an internal model of the circuit model. For example, the circuit data can be indicative of information for circuit parameters determined based on signal transmissions between voxels of the circuit model. In an embodiment, the circuit model optimization component 402 can parameterize the circuit model based on the circuit data. For instance, the circuit model optimization component 402 can parameterize the circuit model based on the circuit properties for the circuit model and/or the circuit parameters associated with the simulation of the internal of the circuit model. In an aspect, the circuit model optimization component 402 can generate and/or modify one or more parameters for the circuit model based on the circuit data.

Figure 5:
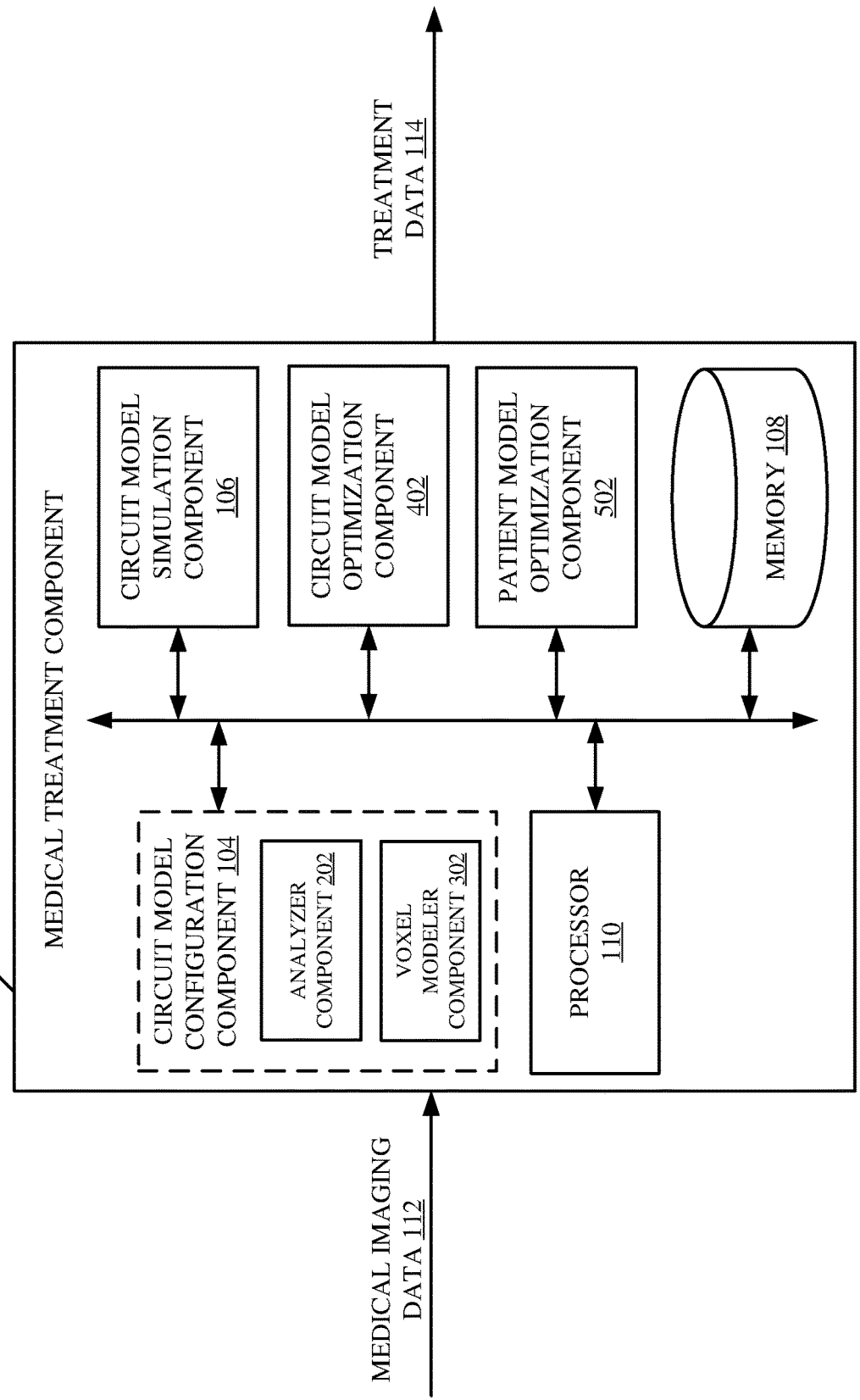
FIG. 5 illustrates a block diagram of yet another example, non-limiting system that includes a medical treatment component in accordance with one or more embodiments described herein.

FIG. 5 illustrates a block diagram of an example, non-limiting system 500 in accordance with one or more embodiments described herein. Repetitive description of like elements employed in other embodiments described herein is omitted for sake of brevity.

The system 500 includes the medical treatment component 102. The medical treatment component 102 can include the circuit model configuration component 104, the circuit model simulation component 106, the circuit model optimization component 402, a patient model optimization component 502, the memory 108 and/or the processor 110. In the embodiment shown in FIG. 5, the circuit model configuration component 104 can include the analyzer component 202 and/or the voxel modeler component 302. The patient model optimization component 502 can be employed to optimize the circuit model based on patient data. The patient data can include information related to a patient identity associated with the circuit model, a patient cohort associated with the circuit model and/or a patient genotypic marker associated with the circuit model. For example, the patient data can include a set of characteristics and/or a set of physical expressions to provide a phenotype profile for a patient identity associated with the circuit model, a patient cohort associated with the circuit model and/or a patient genotypic marker associated with the circuit model. Additionally or alternatively, the patient data can include information related to symptom properties for a patient identity associated with the circuit model, a patient cohort associated with the circuit model and/or a patient genotypic marker associated with the circuit model. The symptom properties can be associated with characteristics of a brain region, a neuron and/or a receptor. For example, the symptom properties can include firing rates for a receptor, inter-spike interval distributions for a receptor, frequency of oscillations associated with a receptor, a power spectra associated with a receptor, and/or other information related to a characteristic of a brain region, a neuron and/or a receptor. In an embodiment, the patient model optimization component 502 can parameterize the circuit model based on the patient data. For instance, the patient model optimization component 502 can parameterize the circuit model based on the information related to the patient identity, the patient cohort, the patient genotypic marker and/or the information related to the symptom properties. In an aspect, the patient model optimization component 502 can generate and/or modify one or more parameters for the circuit model based on the patient data.

Figure 6:
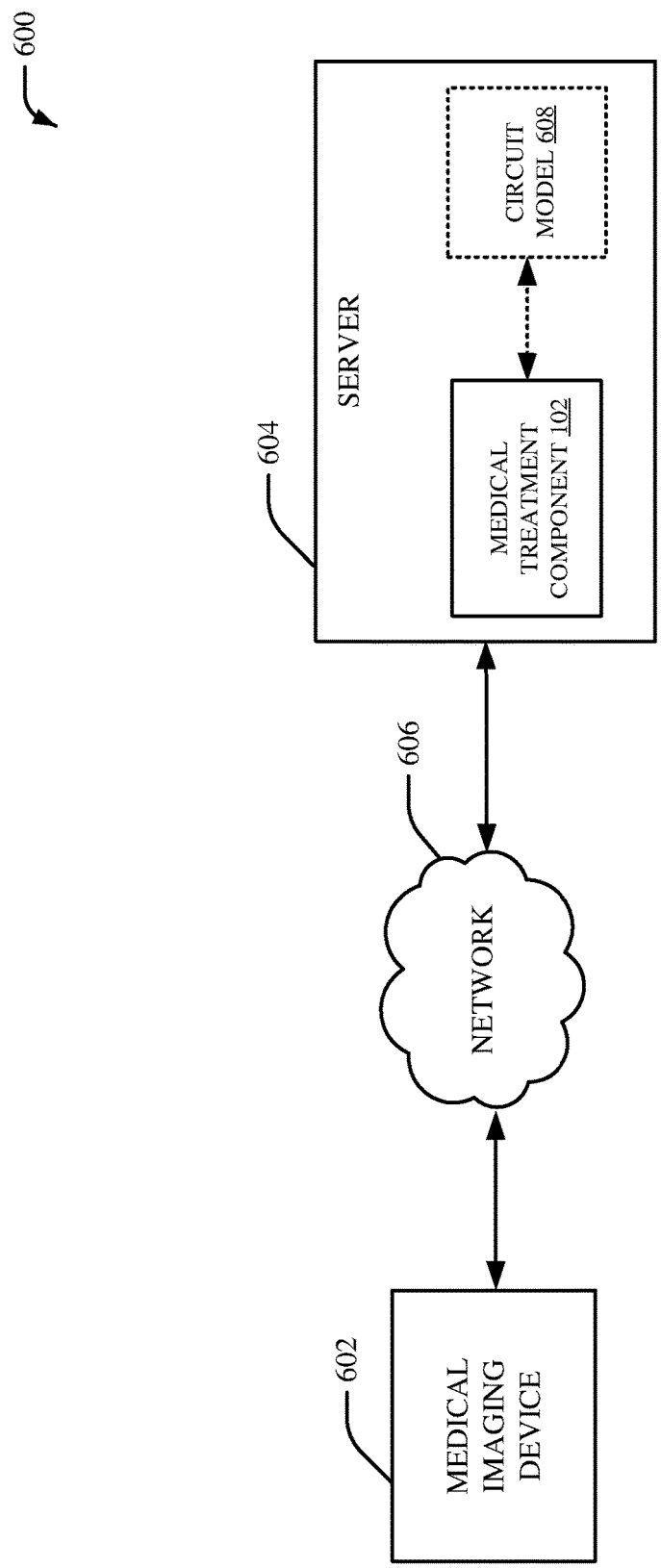
FIG. 6 illustrates an example, non-limiting system that facilitates altering a targeted brain therapeutic based on a brain circuit model in accordance with one or more embodiments described herein.

FIG. 6 illustrates an example, non-limiting system 600 in accordance with one or more embodiments described herein. Repetitive description of like elements employed in other embodiments described herein is omitted for sake of brevity.

The system 600 can be, for example, a network environment (e.g., a network computing environment). The system 600 includes a medical imaging device 602, a server 604 and a network 606. The server 604 can include the medical treatment component 102. The medical treatment component 102 can include the circuit model configuration component 104, the circuit model simulation component 106, the analyzer component 202, the voxel modeler component 302, the circuit model optimization component 402, the patient model optimization component 502, the memory 108 and/or the processor 110. Furthermore, the server 604 can manage a circuit model 608 generated by the medical treatment component 102. The server 604 can be in communication with the medical imaging device 602 via the network 606. For example, the medical treatment component 102 of the server 604 can be in communication with the medical imaging device 602 via the network 606. The network 606 can be a communication network, a wireless network, a wired network, an internet protocol (IP) network, a voice over IP network, an internet telephony network, a mobile telecommunications network or another type of network. The medical imaging device 602 can be one or more medical imaging devices 602. For example, in an embodiment, the server 604 can be in communication with a medical imaging device. In another embodiment, the server 604 can be in communication with two or more medical imaging devices. The medical imaging device 602 can include a set of sensors to facilitate generation of the medical imaging data 112. For example, the medical imaging device 602 can generate at least a portion of the medical imaging data 112. The medical imaging device 602 can be one or more PET devices, one or more CT devices, one or more MRI devices, one or more CAT devices, one or more ultrasound devices, and/or another type of medical imaging device.

In an embodiment, the medical treatment component 102 of the server 604 can receive at least a portion of the medical imaging data 112 from the medical imaging device 602. For example, the medical treatment component 102 of the server 604 can receive at least a portion of the medical imaging data 112 via the network 606. In another embodiment, the medical treatment component 102 of the server 604 (e.g., the circuit model configuration component 104) can determines parameter data associated with the circuit model 608 based on receptor pattern data indicative of receptor expression levels associated with the medical imaging data 112 received from the medical imaging device 602. Furthermore, the medical treatment component 102 of the server 604 (e.g., the circuit model simulation component 106) can simulate the circuit model 608 based on the parameter data to generate the treatment data 114. The circuit model 608 can be a circuit model of a biological brain associated with a patient identity. For example, the circuit model 608 can be a brain circuit model that simulates behavior of a biological brain associated with a patient identity. In an aspect, the circuit model 608 can simulate transmission of signals between brain areas, neurons and/or receptors of a biological brain associated with a patient identity.

Figure 7A:
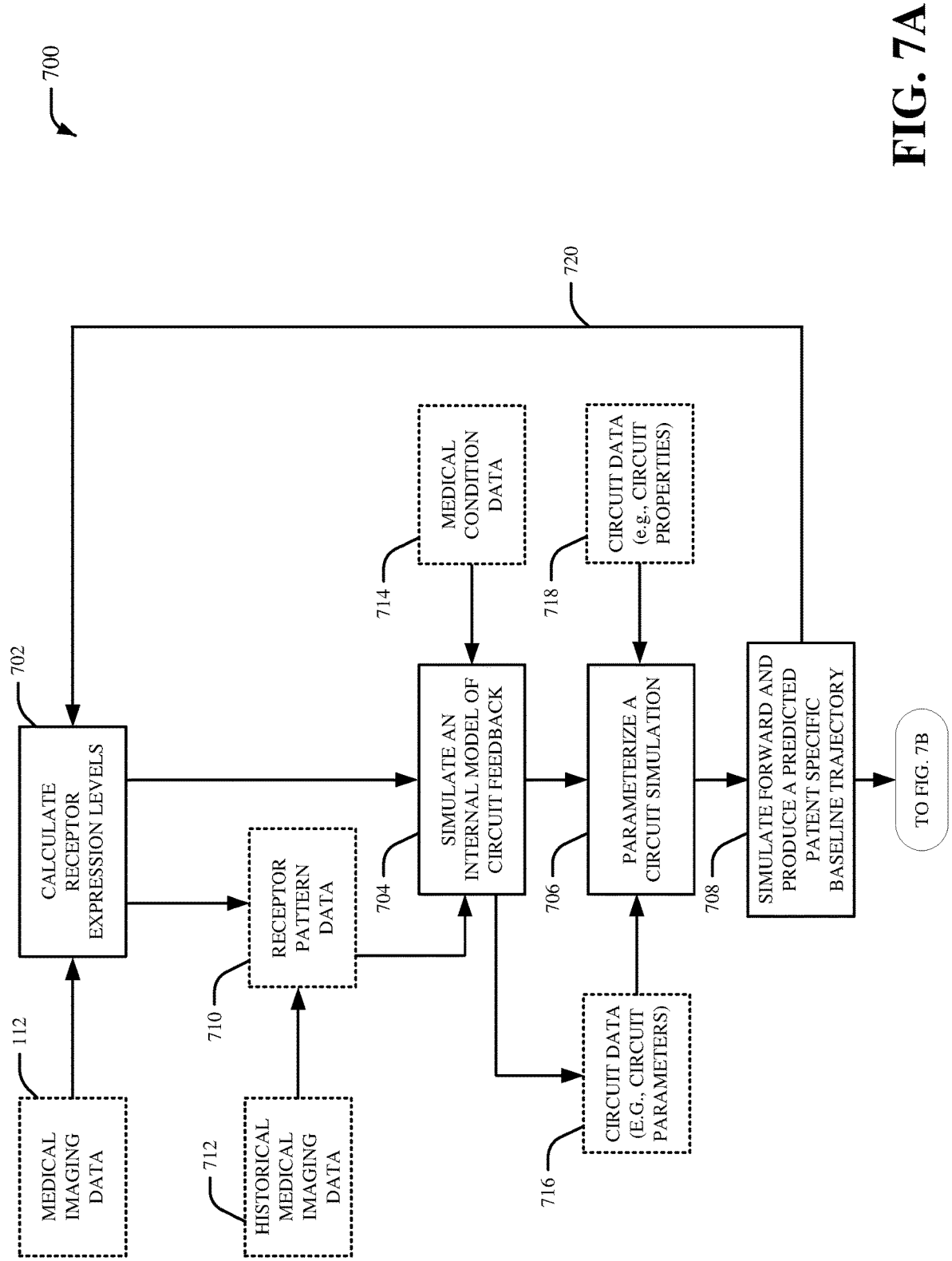
FIG. 7A illustrates an example, non-limiting system that facilitates performing processes for altering a targeted brain therapeutic based on a brain circuit model in accordance with one or more embodiments described herein.

FIG. 7A illustrates an example, non-limiting system 700 in accordance with one or more embodiments described herein. Repetitive description of like elements employed in other embodiments described herein is omitted for sake of brevity.

The system 700 can include a process 702, a process 704, a process 706 and/or a process 708. For example, the process 702, the process 704, process 706 and/or the process 708 can be performed by the medical treatment component 102 (e.g., by the circuit model configuration component 104, the circuit model simulation component 106, the circuit model optimization component 402 and/or the patient model optimization component 502). In an embodiment, the process 702 can calculate receptor expression levels. The process 702 can calculate the receptor expression levels by analyzing the medical imaging data 112. For example, the process 702 can calculate the receptor expression levels by analyzing respective voxels of the medical imaging data 112 and determining respective receptor expression levels for the respective voxels. In an aspect, receptor pattern data 710 can be generated based on the process 702 that calculates the receptor expression levels. The receptor pattern data 710 can be indicative of the receptor expression levels associated with the medical imaging data 112. In certain embodiments, historical medical imaging data 712 can be additionally employed to generate the receptor pattern data 710. The historical medical imaging data 712 can include, for example, one or more PET imagery scans associated with a normal biological brain, one or more PET imagery scans associated with a biological brain related to a medical condition, historical receptor expression levels, and/or other historical information to facilitate generation of the receptor pattern data 710. The process 704 can simulate an internal model of circuit feedback based on the process 702. For example the process 704 can employ the receptor pattern data 710 and/or medical condition data 714 to simulate the internal model of the circuit feedback. In an aspect, the process 704 can simulate transmission of signals between brain areas, neurons and/or receptors in a circuit model of a biological brain related to the medical imaging data 112. For example, the process 704 can simulate interaction of receptors and/or voxels. The process 704 can also simulate excitatory neurotransmissions and/or inhibitory neurotransmissions between brain areas, neurons and/or receptors. In another aspect, control of receptor expression levels associated with the receptor pattern data 710 can be simulated based on constraints of measured receptor expression levels. The medical condition data 714 can be indicative of information for properties associated with one or more medical conditions. In an aspect, the medical condition data 714 can be related to one or more internal model properties of a circuit model. The one or more internal model properties of the medical condition data 714 can also be directly relevant to one or more medical conditions. For instance, the one or more internal model properties of the medical condition data 714 can be one or more cell properties related to one or more medical conditions. In an example, the one or more internal model properties of the medical condition data 714 can be one or more cell properties related to a first medical condition, one or more other cell properties related to a second medical condition, etc. The one or more internal model properties (e.g., the one or more cell properties) of the medical condition data 714 can include data associated with intrinsic cell excitability, data associated with cell channel properties, data associated with cell type, etc.

The process 706 can parameterize a circuit simulation based on the process 704. For example, the process 706 can employ circuit data 716 and/or circuit data 718 to parameterize the circuit simulation. The circuit data 716 can be circuit data that is different than the circuit data 718. For example, the circuit data 716 can be parameter data that includes one or more circuit parameters to facilitate the circuit simulation of a circuit model. Furthermore, the circuit data 718 can be one or more circuit properties to additionally or alternatively facilitate the circuit simulation of a circuit model. In an embodiment, the circuit data 716 can be indicative of information for circuit parameters associated with simulation of an internal model of the circuit model. For example, the circuit data 716 can be indicative of information for circuit parameters determined based on signal transmissions between voxels and/or receptors of the circuit model. In another example, the circuit data 716 can be a set of circuit parameters predicted from the process 704 associated with the simulation of the internal model. For instance, the set of circuit parameters can include total excitation received by dendrites of neurons associated with a voxel of the medical imaging data 112 that are consistent with the measured receptor expression level associated with the receptor pattern data 710, total inhibition received by dendrites of neurons associated with a voxel of the medical imaging data 112 that are consistent with the measured receptor expression level associated with the receptor pattern data 710, etc. In another embodiment, the circuit data 718 can be indicative of information for circuit properties associated with a patient identity, a patient cohort and/or a patient genotypic marker. For example, the circuit data 718 can be patient data related to symptom properties for a patient identity associated with the circuit model, a patient cohort associated with the circuit model, and/or a patient genotypic marker associated with the circuit model. The circuit data 718 can be associated with characteristics of a receptor. For example, the circuit data 718 can include firing rates for a receptor, inter-spike interval distributions for a receptor, frequency of oscillations associated with a receptor, a power spectra associated with a receptor, and/or other information related to a characteristic of a receptor. The process 708 can simulate forward and produce a patient specific baseline trajectory based on the process 706. For example, the process 708 can perform a forward simulation associated with machine learning to calculate a patient specific baseline trajectory. In an aspect, the process 708 can simulate the circuit model. The patient specific baseline trajectory can be a baseline trajectory pattern for a particular patient identity associated with the circuit model and/or the medical imaging data 112. In an example, the patient specific baseline trajectory can be a simulated pattern for one or more receptors associated with a biological brain of the particular patient identity. In certain embodiments, data associated with the process 708 can be provided to the process 702 via a feedback loop 720. In certain embodiments, the process 702, the process 704, the process 706 and/or the process 708 can be repeated one or more times for additional medical imaging data. For example, the simulation can be optimized with a population parameter search technique that determines optimal parameters for the simulation. In certain embodiments, the process 702 can be performed by a PET analyzer, the process 704 can be performed by a PET voxel modeler, the process 706 can be performed by a circuit model optimizer and/or a patient model optimizer, and/or the process 708 can be performed by a circuit modeler.

Figure 7B:
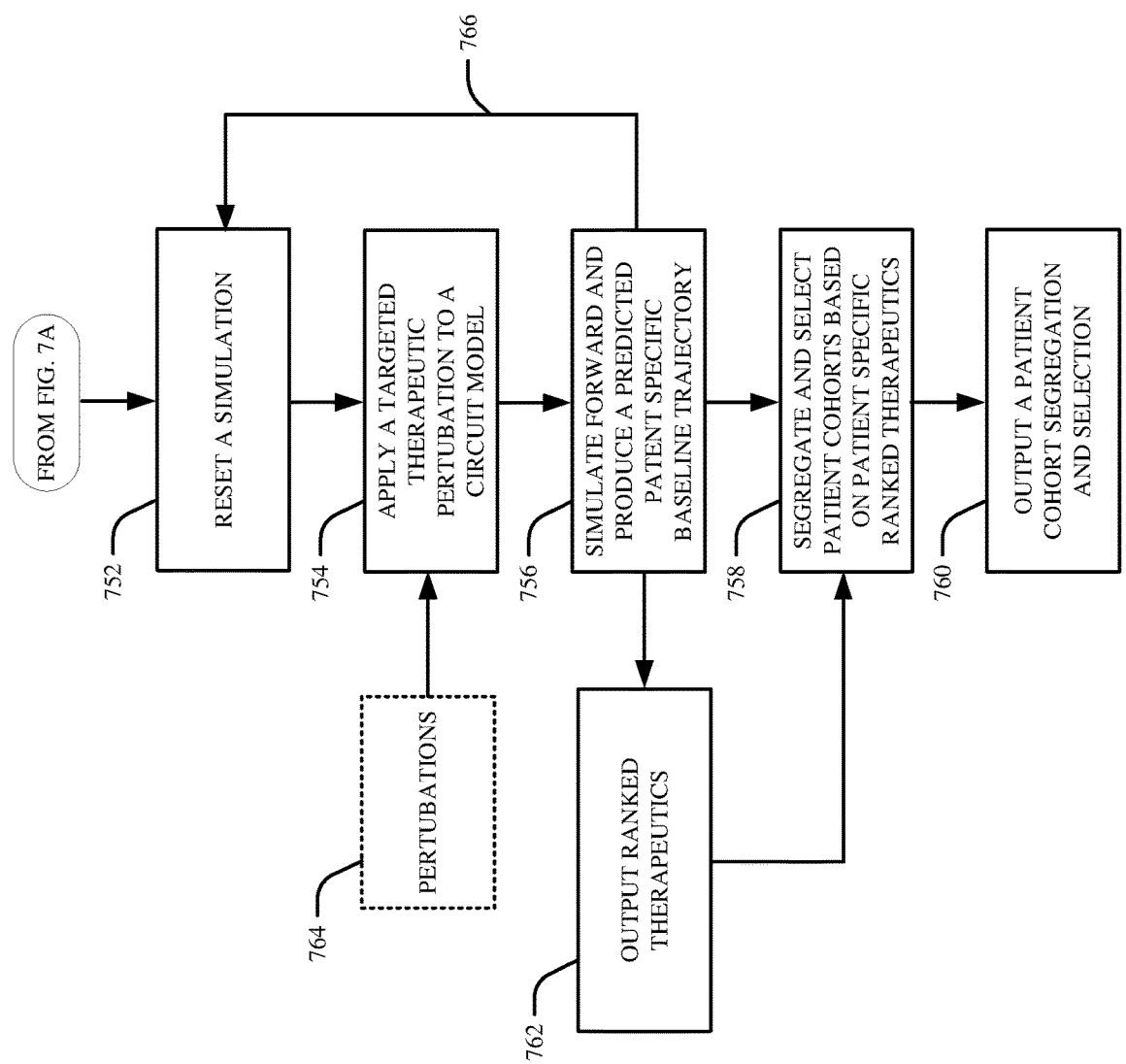
FIG. 7B illustrates another example, non-limiting system that facilitates performing processes for altering a targeted brain therapeutic based on a brain circuit model in accordance with one or more embodiments described herein.

FIG. 7B illustrates an example, non-limiting system 750 in accordance with one or more embodiments described herein. Repetitive description of like elements employed in other embodiments described herein is omitted for sake of brevity.

The system 750 can be related to the system 700. For example, the system 750 can include a process 752, a process 754, a process 756, a process 758, a process 760 and/or a process 762 that can be performed after the process 708 shown in FIG. 7A. For example, the process 752, the process 754, the process 756, the process 758, the process 760 and/or the process 762 can be performed by the medical treatment component 102 (e.g., by the circuit model configuration component 104, the circuit model simulation component 106, the circuit model optimization component 402 and/or the patient model optimization component 502). In an embodiment, the process 752 can reset a simulation. For example, the process 752 can reset a simulation associated with the process 708. The process 754 can apply a targeted therapeutic perturbation to a circuit model. For example, perturbations 764 can be a set of perturbations (e.g., a set of therapeutic perturbations) of potential inputs for the circuit model. In an aspect, the perturbations 764 can include different arrangements (e.g., different combinations) of input parameter values for the circuit model. In another aspect, the targeted therapeutic perturbation can include treatment data associated with a treatment type and/or a treatment location for a medical condition. The process 756 can simulate forward and produce a patient specific baseline trajectory based on the process 754. For example, the process 756 can perform a forward simulation associated with machine learning to calculate a patient specific baseline trajectory. In an aspect, the process 756 can simulate the circuit model. The patient specific baseline trajectory can be a baseline trajectory pattern for a particular patient identity associated with the circuit model and/or the medical imaging data 112. In an example, the patient specific baseline trajectory can be a simulated pattern for one or more receptors associated with a biological brain of the particular patient identity. In certain embodiments, data associated with the process 756 can be provided to the process 752 via a feedback loop 766. In certain embodiments, the process 752, the process 754 and/or the process 756 can be repeated one or more times for additional medical imaging data. Based on the process 756, the process 758 can segregate and select patient cohorts based on patient specific ranked therapeutics. The patient cohorts can be sample groupings of treatment data for different treatments associated with a medical condition. For example, the patient cohorts can be sample groupings of treatment data for different treatment types and/or different treatment locations. The process 760 can output a patient cohort segregation and selection. For example, the process 760 can output an optimal patient cohort segregation and selection. In an aspect, the process 760 can output an treatment type and/or an optimal treatment location for a medical condition. In certain embodiments, the process 762 can output ranked therapeutics based on the process 756. For example, a ranking of different treatments for a medical condition and/or a ranking of different treatment locations for a medical condition can be output. In certain embodiments, the process 752, the process 754, the process 756 and/or the process 762 can be associated with therapeutic design. Additionally, the process 758 and/or the process 760 can be associated with prognostic enrichment.

Figure 8:
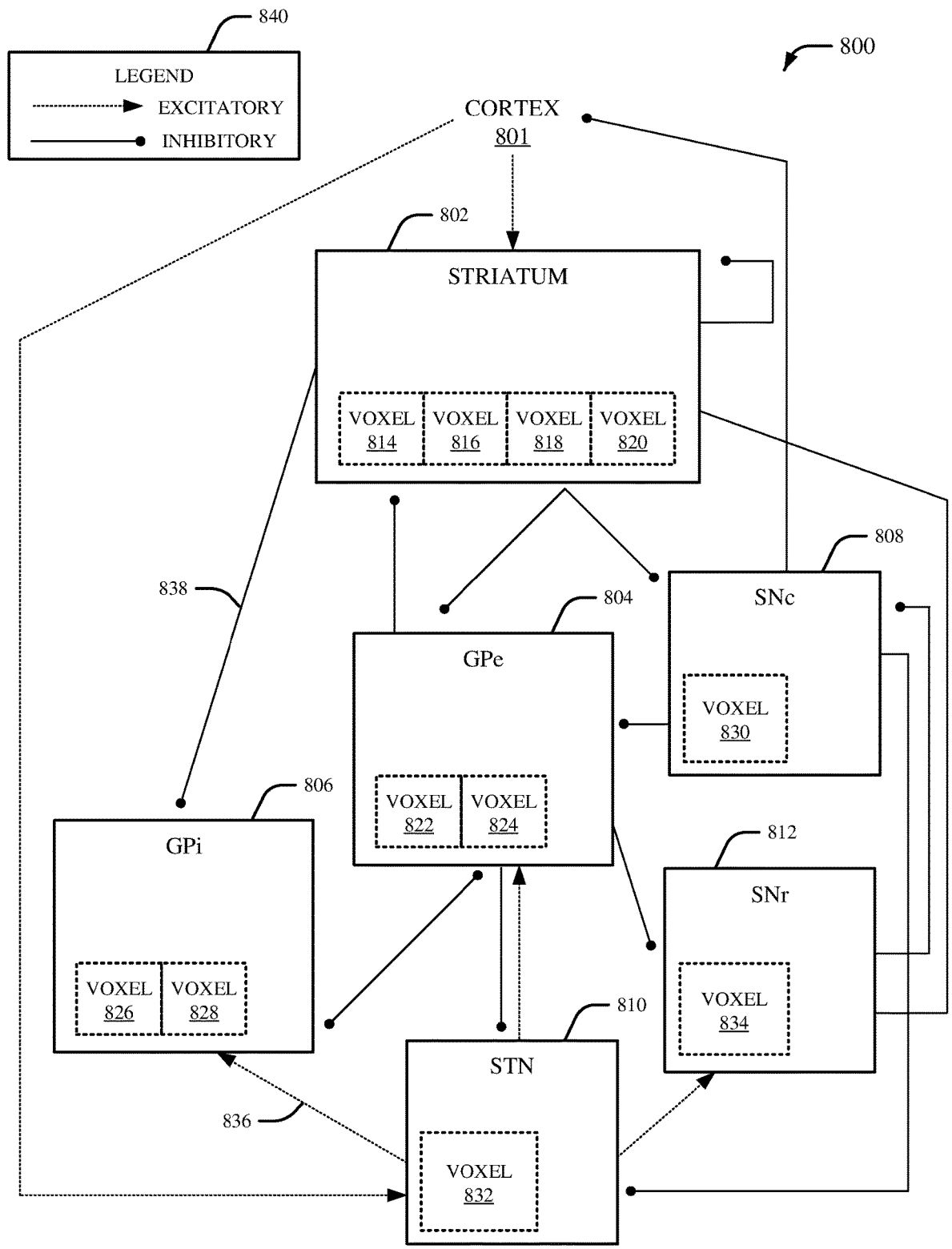
FIG. 8 illustrates an example, non-limiting system associated with a circuit model in accordance with one or more embodiments described herein.

FIG. 8 illustrates an example, non-limiting system 800 in accordance with one or more embodiments described herein. Repetitive description of like elements employed in other embodiments described herein is omitted for sake of brevity.

The system 800 can illustrate an example circuit model (e.g., an example brain circuit model). For example, the system 800 can be an example circuit model of basal ganglia comprised of numerous voxels with constraints determined by a voxel modeler (e.g., determined by the circuit model configuration component 104 and/or the voxel modeler component 302). The system 800 can include a brain area 802, a brain area 804, a brain area 806, a brain area 808, a brain area 810 and/or a brain area 812. The brain area 802 can be, for example, a model (e.g., an internal model) of a Striatum nucleus of a biological brain. Furthermore, the brain area 802 can include as set of voxels (e.g., a voxel 814, a voxel 816, a voxel 818 and a voxel 820). The brain area 804 can be, for example, a model (e.g., an internal model) of an external globus pallidus (GPe) structure of a biological brain. Furthermore, the brain area 804 can include as set of voxels (e.g., a voxel 822 and a voxel 824). The brain area 806 can be, for example, a model (e.g., an internal model) of an globus pallidus (GPi) structure of a biological brain. Furthermore, the brain area 806 can include as set of voxels (e.g., a voxel 826 and a voxel 828). The brain area 808 can be, for example, a model (e.g., an internal model) of a substantia nigra pars compacta (SNc) structure of a biological brain. Furthermore, the brain area 808 can include as set of voxels (e.g., a voxel 830). The brain area 810 can be, for example, a model (e.g., an internal model) of a subthalamic nucleus (STN) nucleus of a biological brain. Furthermore, the brain area 810 can include as set of voxels (e.g., a voxel 832). The brain area 812 can be, for example, a model (e.g., an internal model) of a substantia nigra (SNr) nucleus of a biological brain. Furthermore, the brain area 812 can include as set of voxels (e.g., a voxel 34). The system 800 can also include a cortex 801. The cortex 801 can be a cortex structure of a biological brain. In an embodiment, the system 800 can illustrate neurotransmissions between the cortex 801, the brain area 802, the brain area 804, the brain area 806, the brain area 808, the brain area 810 and/or the brain area 812. For instance, the circuit model associated with the system 800 can simulate excitatory neurotransmission and/or inhibitory neurotransmission between the cortex 801, the brain area 802, the brain area 804, the brain area 806, the brain area 808, the brain area 810 and/or the brain area 812. For example, an excitatory neurotransmission 836 can be transmitted between the brain area 810 and the brain area 806. In another example, an inhibitory neurotransmission 838 can be transmitted between the brain area 802 and the brain area 806. In an embodiment, the neurotransmissions between the cortex 801, the brain area 802, the brain area 804, the brain area 806, the brain area 808, the brain area 810 and/or the brain area 812 can be determined by the circuit model simulation component 106. In another embodiment, the brain area 802, the brain area 804, the brain area 806, the brain area 808, the brain area 810 and/or the brain area 812 can be constrained and/or configured using respective parameters. Additionally, the system 800 includes a legend 840 for illustrative purposes to illustrate formatting of an excitatory neurotransmission and formatting of an inhibitory neurotransmission, as shown in FIG. 8.

Figure 9:
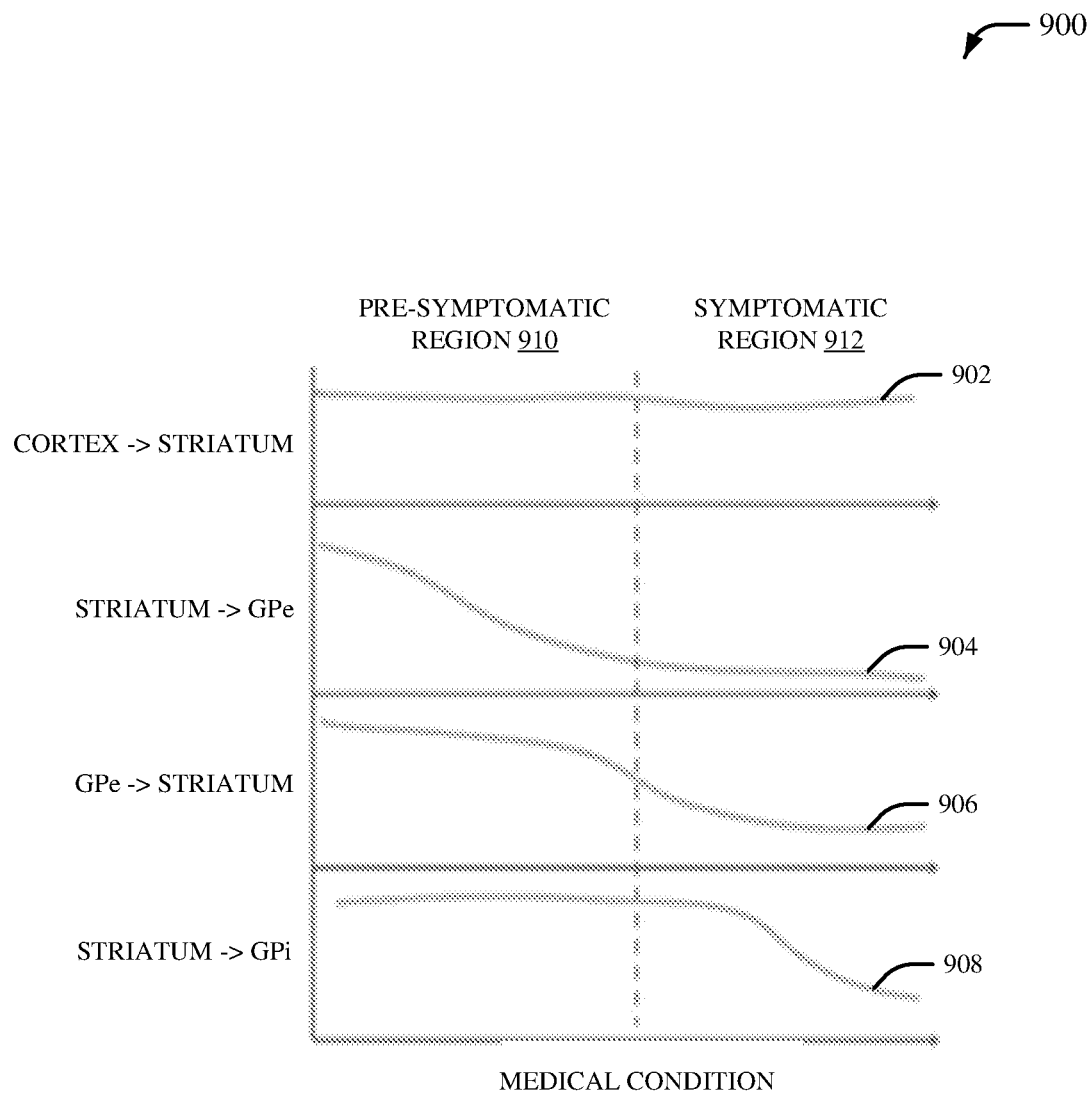
FIG. 9 illustrates an example, non-limiting graph associated with altering a targeted brain therapeutic in accordance with one or more embodiments described herein.

FIG. 9 illustrates an example, non-limiting graph 900 in accordance with one or more embodiments described herein. Repetitive description of like elements employed in other embodiments described herein is omitted for sake of brevity.

The graph 900 can illustrate a patient specific baseline trajectory 902, a patient specific baseline trajectory 904, a patient specific baseline trajectory 906 and a patient specific baseline trajectory 908. For example, the patient specific baseline trajectory 902 can be a patient specific baseline trajectory for a connection between the cortex 901 and the brain area 802 (e.g., between a cortex and a striatum). In an aspect, the patient specific baseline trajectory 902 can be a simulated pattern that is represented as a function of a medical condition (e.g., progression of a medical condition over time) and the connection between the cortex 901 and the brain area 802. The patient specific baseline trajectory 904 can be, for example, a patient specific baseline trajectory for a connection between the cortex 901 and the brain area 804 (e.g., between a cortex and a GPe). In an aspect, the patient specific baseline trajectory 902 can be a simulated pattern that is represented as a function of a medical condition (e.g., progression of a medical condition over time) and the connection between the cortex 901 and the brain area 804. The patient specific baseline trajectory 906 can be, for example, a patient specific baseline trajectory for a connection between the brain area 804 and the cortex 901 (e.g., between a GPe and a striatum). In an aspect, the patient specific baseline trajectory 902 can be a simulated pattern that is represented as a function of a medical condition (e.g., progression of a medical condition over time) and the connection between the brain area 804 and the cortex 901. Furthermore, the patient specific baseline trajectory 904 can be, for example, a patient specific baseline trajectory for a connection between the cortex 901 and the brain area 806 (e.g., between a cortex and a GPi). In an aspect, the patient specific baseline trajectory 902 can be a simulated pattern that is represented as a function of a medical condition (e.g., progression of a medical condition over time) and the connection between the cortex 901 and the brain area 806. In an aspect, the graph 800 can include a pre-symptomatic region 910 that illustrates a characterization of a portion of the patient specific baseline trajectory 902, the patient specific baseline trajectory 904, the patient specific baseline trajectory 906 and/or the patient specific baseline trajectory 908 for a pre-symptomatic period of a medical condition progression. The graph 800 can also include a symptomatic region 912 that illustrates a characterization of another portion of the patient specific baseline trajectory 902, the patient specific baseline trajectory 904, the patient specific baseline trajectory 906 and/or the patient specific baseline trajectory 908 for a symptomatic period of a medical condition progression.

Figure 10:
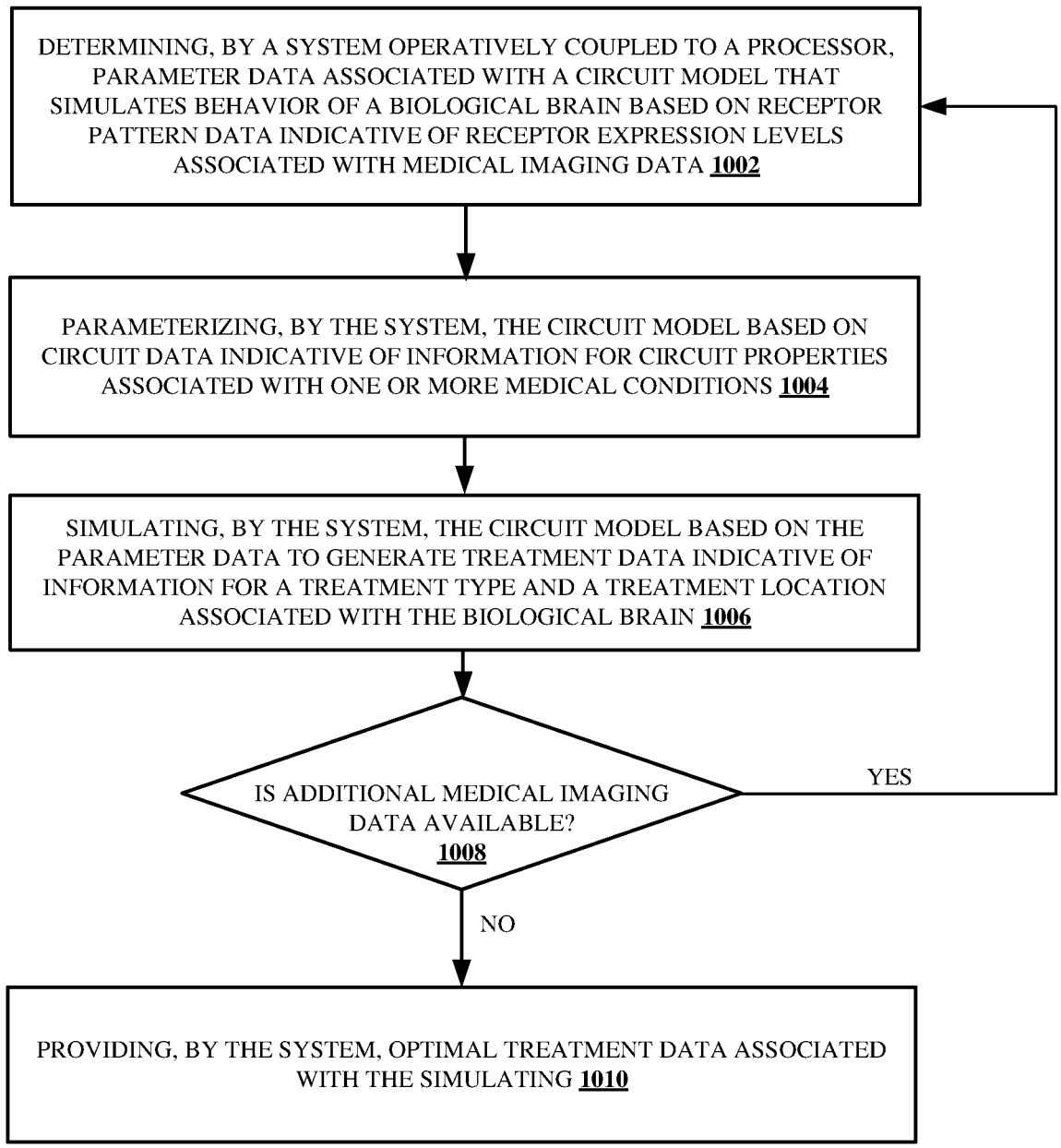
FIG. 10 illustrates a flow diagram of an example, non-limiting computer-implemented method for facilitating altering a targeted brain therapeutic in accordance with one or more embodiments described herein.

FIG. 10 illustrates a flow diagram of an example, non-limiting computer-implemented method 1000 for altering a targeted brain therapeutic based on a brain circuit model in accordance with one or more embodiments described herein. At 1002, parameter data associated with a circuit model that simulates behavior of a biological brain is determined, by a system operatively coupled to a processor (e.g., by circuit model configuration component 104), based on receptor pattern data indicative of receptor expression levels associated with medical imaging data. For example, the parameter data can include one or more circuit parameters to facilitate the circuit simulation of the circuit model. Furthermore, the parameter data can be indicative of information for circuit parameters determined based on signal transmissions between voxels and/or receptors of the circuit model. The circuit model can be a circuit model of a biological brain associated with a patient identity. For example, the circuit model can be a brain circuit model that simulates behavior of a biological brain associated with a patient identity. In an aspect, the circuit model can simulate transmission of signals between brain areas of a biological brain associated with a patient identity. The receptor pattern data can be indicative of the receptor expression levels associated with the medical imaging data. Furthermore, the medical imaging data can be medical imagery associated with image pixel data. For example, the medical imaging data can be medical imagery where respective radioactivity concentration values are assigned to respective image pixels. The medical imaging data can be generated by one or more medical imaging devices associated with a set of sensors. A medical imaging device from the one or more medical imaging devices can be a PET device, a CT device, a MRI device, a CAT device, an ultrasound device, or another type of medical imaging device.

At 1004, the circuit model is parameterized, by the system (e.g., by circuit model configuration component 104), based on circuit data indicative of information for circuit properties associated with one or more medical conditions. For example one or more parameters for the circuit model can be modified and/or added based on the circuit data. The circuit properties associated with the circuit data can be associated with characteristics of a brain region, a neuron and/or a receptor. For example, the circuit properties can include firing rates for a receptor, inter-spike interval distributions for a receptor, frequency of oscillations associated with a receptor, a power spectra associated with a receptor, and/or other information related to a characteristic of a brain region, a neuron and/or receptor.

At 1006, the circuit model is simulated, by the system (e.g., by circuit model simulation component 106), based on the parameter data to generate treatment data indicative of information for a treatment type and a treatment location associated with the biological brain. For example, one or more machine learning techniques can be performed based on the parameter data to generate the treatment data.

At 1008, it is determined whether additional medical imaging data is available. If yes, the computer-implemented method 1000 can return to 1002. If no, the computer-implemented method 1000 can proceed to 1010.

At 1010, optimal treatment data associated with the simulating is provided by the system (e.g., by circuit model simulation component 106). For example, the optimal treatment data can be provided to a display of an electronic device in a human-interpretable format. The electronic device can be a screen, a monitor, a projector wall, a user device, a desktop computer, a laptop computer, a smart device, a smart phone, a mobile device, a handheld device, a tablet device, a virtual reality device, a portable computing device, or another display device associated with a display configured to present information associated with the optimal treatment data in a human-interpretable format. In certain embodiments, the optimal treatment data can be provided to a medical imaging device and/or another medical device to alter one or more settings and/or one or more parameters of the medical imaging device and/or the other medical device. As such, the optimal treatment data can be provided to an external system. In certain embodiments, the determining the parameter data can comprise facilitating determination of an improved circuit model.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Moreover, because at least analyzing the simulating the circuit model, etc. are established from a combination of electrical and mechanical components and circuitry, a human is unable to replicate or perform a condition detection process associated with the medical treatment component 102 (e.g., the circuit model configuration component 104, the circuit model simulation component 106, the circuit model optimization component 402 and/or the patient model optimization component 502) disclosed herein. For example, a human is unable to perform a simulation process, a human is unable to perform machine learning, etc.

Figure 11:
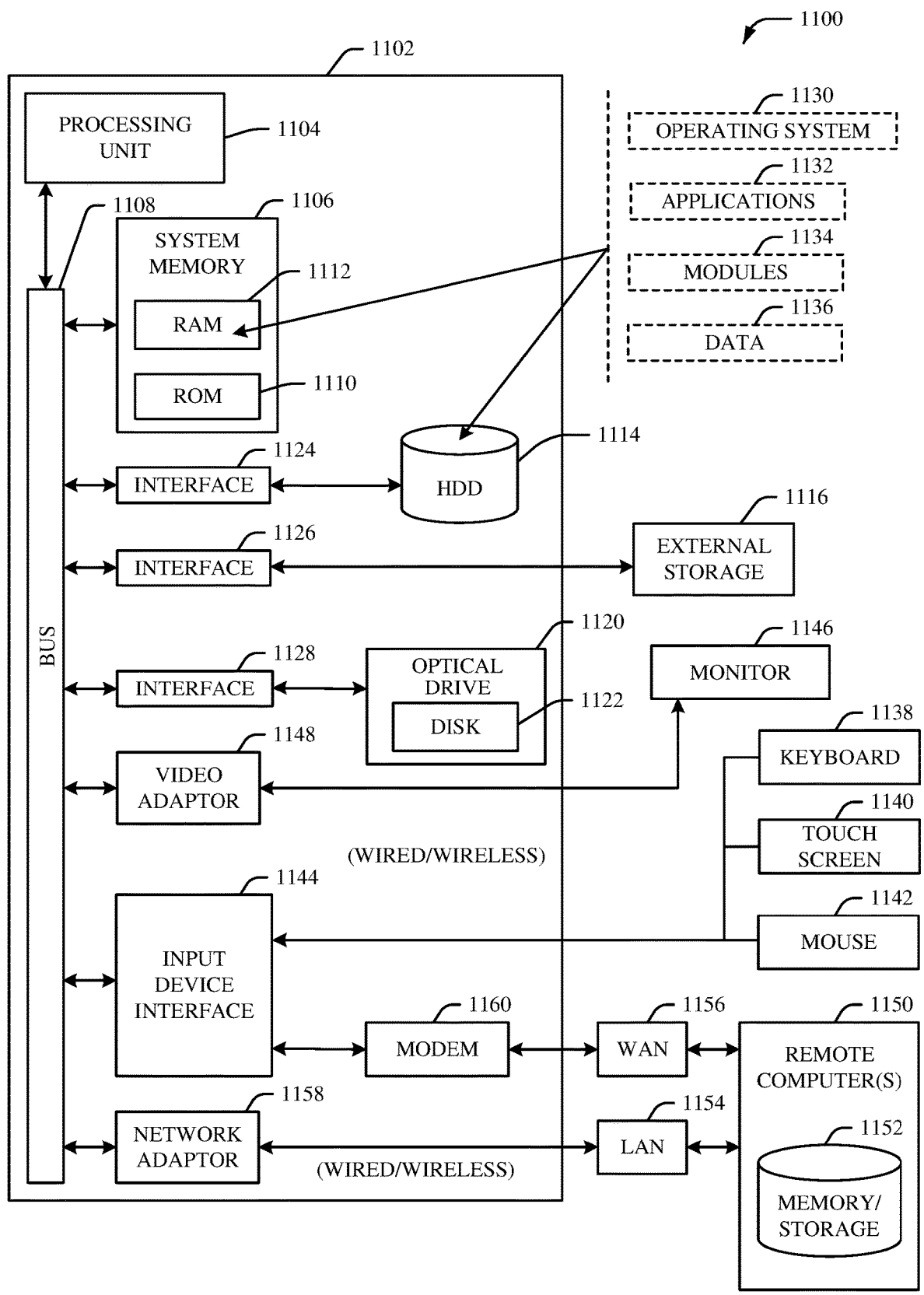
FIG. 11 illustrates a block diagram of an example, non-limiting operating environment in which one or more embodiments described herein can be facilitated.

In order to provide additional context for various embodiments described herein, FIG. 11 and the following discussion are intended to provide a general description of a suitable computing environment 1100 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, the example environment 1100 for implementing various embodiments of the aspects described herein includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures can also be employed as the processing unit 1104.

The system bus 1108 can be any of several types of bus structure that can further interconnect to a memory bus (with or without a memory controller), a peripheral bus, and a local bus using any of a variety of commercially available bus architectures. The system memory 1106 includes ROM 1110 and RAM 1112. A basic input/output system (BIOS) can be stored in a non-volatile memory such as ROM, erasable programmable read only memory (EPROM), EEPROM, which BIOS contains the basic routines that help to transfer information between elements within the computer 1102, such as during startup. The RAM 1112 can also include a high-speed RAM such as static RAM for caching data.

The computer 1102 further includes an internal hard disk drive (HDD) 1114 (e.g., EIDE, SATA), one or more external storage devices 1116 (e.g., a magnetic floppy disk drive (FDD) 1116, a memory stick or flash drive reader, a memory card reader, etc.) and an optical disk drive 1120 (e.g., which can read or write from a CD-ROM disc, a DVD, a BD, etc.). While the internal HDD 1114 is illustrated as located within the computer 1102, the internal HDD 1114 can also be configured for external use in a suitable chassis (not shown). Additionally, while not shown in environment 1100, a solid state drive (SSD) could be used in addition to, or in place of, an HDD 1114. The HDD 1114, external storage device(s) 1116 and optical disk drive 1120 can be connected to the system bus 1108 by an HDD interface 1124, an external storage interface 1126 and an optical drive interface 1128, respectively. The interface 1124 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. The systems and methods described herein can be implemented utilizing various commercially available operating systems or combinations of operating systems.

Computer 1102 can optionally comprise emulation technologies. For example, a hypervisor (not shown) or other intermediary can emulate a hardware environment for operating system 1130, and the emulated hardware can optionally be different from the hardware illustrated in FIG. 11. In such an embodiment, operating system 1130 can comprise one virtual machine (VM) of multiple VMs hosted at computer 1102. Furthermore, operating system 1130 can provide runtime environments, such as the Java runtime environment or the .NET framework, for applications 1132. Runtime environments are consistent execution environments that allow applications 1132 to run on any operating system that includes the runtime environment. Similarly, operating system 1130 can support containers, and applications 1132 can be in the form of containers, which are lightweight, standalone, executable packages of software that include, e.g., code, runtime, system tools, system libraries and settings for an application.

Further, computer 1102 can be enable with a security module, such as a trusted processing module (TPM). For instance with a TPM, boot components hash next in time boot components, and wait for a match of results to secured values, before loading a next boot component. This process can take place at any layer in the code execution stack of computer 1102, e.g., applied at the application execution level or at the operating system (OS) kernel level, thereby enabling security at any level of code execution.

A user can enter commands and information into the computer 1102 through one or more wired/wireless input devices, e.g., a keyboard 1138, a touch screen 1140, and a pointing device, such as a mouse 1142. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1104 through an input device interface 1144 that can be coupled to the system bus 1108, but can be connected by other interfaces, such as a parallel port, an IEEE 1394 serial port, a game port, a USB port, an IR interface, a BLUETOOTH® interface, etc.

A monitor 1146 or other type of display device can be also connected to the system bus 1108 via an interface, such as a video adapter 1148. In addition to the monitor 1146, a computer typically includes other peripheral output devices (not shown), such as speakers, printers, etc.

The computer 1102 can operate in a networked environment using logical connections via wired and/or wireless communications to one or more remote computers, such as a remote computer(s) 1150. The remote computer(s) 1150 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1152 is illustrated. The logical connections depicted include wired/wireless connectivity to a local area network (LAN) 1154 and/or larger networks, e.g., a wide area network (WAN) 1156. Such LAN and WAN networking environments are commonplace in offices and companies, and facilitate enterprise-wide computer networks, such as intranets, all of which can connect to a global communications network, e.g., the Internet.

When used in a LAN networking environment, the computer 1102 can be connected to the local network 1154 through a wired and/or wireless communication network interface or adapter 1158. The adapter 1158 can facilitate wired or wireless communication to the LAN 1154, which can also include a wireless access point (AP) disposed thereon for communicating with the adapter 1158 in a wireless mode.

When used in a WAN networking environment, the computer 1102 can include a modem 1160 or can be connected to a communications server on the WAN 1156 via other means for establishing communications over the WAN 1156, such as by way of the Internet. The modem 1160, which can be internal or external and a wired or wireless device, can be connected to the system bus 1108 via the input device interface 1144. In a networked environment, program modules depicted relative to the computer 1102 or portions thereof, can be stored in the remote memory/storage device 1152. It will be appreciated that the network connections shown are example and other means of establishing a communications link between the computers can be used.

When used in either a LAN or WAN networking environment, the computer 1102 can access cloud storage systems or other network-based storage systems in addition to, or in place of, external storage devices 1116 as described above. Generally, a connection between the computer 1102 and a cloud storage system can be established over a LAN 1154 or WAN 1156 e.g., by the adapter 1158 or modem 1160, respectively. Upon connecting the computer 1102 to an associated cloud storage system, the external storage interface 1126 can, with the aid of the adapter 1158 and/or modem 1160, manage storage provided by the cloud storage system as it would other types of external storage. For instance, the external storage interface 1126 can be configured to provide access to cloud storage sources as if those sources were physically connected to the computer 1102.

The computer 1102 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, Matlab, Python, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
a circuit model configuration component that:
analyzes, using a machine learning model, medical imaging data comprising one or more positron emission tomography (PET) scans of one or more biological brains to determine respective radioactivity concentrations represented in pixels of the medical imaging data,
determines, using the machine learning model, based on the respective radioactivity concentrations represented in the pixels, receptor pattern data comprising, for each pixel, respective expression levels of different types of brain receptors in the one or more biological brains, and
generates, using the machine learning model, a circuit model of a biological brain using parameter data generated based on the receptor pattern data; and
a circuit model simulation component that simulates, using the machine learning model, changes in circuit properties of the circuit model from applying perturbations to the circuit model based on the parameter data to generate treatment data associated with the biological brain, wherein the perturbations comprise combinations of different treatment types and different treatment locations of the biological brain represented in the circuit model, and the treatment data comprises an optimal treatment type and treatment location selected from the combinations of the different treatment types and the different treatment locations according to a selection criterion.

2. The system of claim 1, wherein the parameter data further comprises transmission data representing signal transmissions between brain areas, neurons, and the brain receptors of the biological brain.

3. The system of claim 1, wherein the circuit model configuration component comprises a voxel modeler component that simulates, using the machine learning model, a set of voxel segments of the medical imaging data to generate the parameter data.

4. The system of claim 3, wherein the voxel modeler component simulates, using the machine learning model, the set of voxel segments based on medical condition data indicative of information for properties associated with at least one medical condition.

5. The system of claim 3, wherein the voxel modeler component simulates, using the machine learning model, the set of voxel segments based on medical condition data indicative of information for properties associated with a normal range for at least one medical condition.

6. The system of claim 1, wherein the different types of brain receptors comprise at least one of a cannabinoid receptor, a receptor associated with a norepinephrine transporter, a dopamine receptor, an inhibitory receptor, a nicotinic receptor, or a receptor associated with beta-amyloid plaque.

7. The system of claim 1, wherein the computer executable components comprise:
a circuit model optimization component that parameterizes, using the machine learning model, the circuit model based on circuit data indicative of information for the circuit properties associated with at least one medical condition.

8. The system of claim 1, wherein the computer executable components comprise:
a patient model optimization component that parameterizes, using the machine learning model, the circuit model based on circuit data indicative of information for the circuit properties associated with at least one of a patient identity, a patient cohort, and a patient genotypic marker.

9. The system of claim 1, wherein the circuit model simulation component repeats simulation based on availability of the medical imaging data.

10. The system of claim 1, wherein the circuit model simulation component ranks the combinations of the different treatment types and the different treatment locations.

11. The system of claim 1, wherein the circuit model configuration component determines the parameter data to facilitate generation of an improved circuit model.

12. A computer-implemented method, comprising:
analyzing, by a system operatively coupled to a processor, using a machine learning model, medical imaging data comprising one or more PET scans of one or more biological brains to determine respective radioactivity concentrations represented in pixels of the medical imaging data;
determining, by the system, using the machine learning model, based on the respective radioactivity concentrations represented in the pixels, receptor pattern data comprising, for each pixel, respective expression levels of different types of brain receptors in the one or more biological brains;
generating, by the system, using the machine learning model, a circuit model of a biological brain using parameter data generated based on the receptor pattern data; and
simulating, by the system, using the machine learning model, changes in circuit properties of the circuit model from applying perturbations to the circuit model based on the parameter data to generate treatment data associated with the biological brain, wherein the perturbations comprise combinations of different treatment types and different treatment locations of the biological brain represented in the circuit model, and the treatment data comprises an optimal treatment type and treatment location selected from the combinations of the different treatment types and the different treatment locations according to a selection criterion.

13. The method of claim 12, further comprising:
determining, by the system, whether additional medical imaging data is available.

14. The method of claim 13, further comprising:
in response to determining that the additional medical imaging data is available, repeating the simulating.

15. The method of claim 14, further comprising:
in response to determining that the additional medical imaging data is not available, providing the treatment data to an external system.

16. The method of claim 12, wherein the different types of brain receptors comprise at least one of a cannabinoid receptor, a receptor associated with a norepinephrine transporter, a dopamine receptor, an inhibitory receptor, a nicotinic receptor, or a receptor associated with beta-amyloid plaque.

17. A computer program product facilitating altering a targeted brain therapeutic, the computer program product comprising a computer readable storage medium having program instructions embodied therewith, the program instructions executable by a processor to cause the processor to:
analyze, by the processor, using a machine learning model, medical imaging data comprising one or more PET scans of one or more biological brains to determine respective radioactivity concentrations represented in pixels of the medical imaging data;
determine, by the processor, using the machine learning model, based on the respective radioactivity concentrations represented in the pixels, receptor pattern data comprising, for each pixel, respective expression levels of different types of brain receptors in the one or more biological brains;
generate, by the processor, using the machine learning model, a circuit model of a biological brain using parameter data generated based on the receptor pattern data; and
simulate, by the processor, using the machine learning model, changes in circuit properties of the circuit model from applying perturbations to the circuit model based on the parameter data to generate treatment data associated with the biological brain, wherein the perturbations comprise combinations of different treatment types and different treatment locations of the biological brain represented in the circuit model, and the treatment data comprises an optimal treatment type and treatment location selected from the combinations of the different treatment types and the different treatment locations according to a selection criterion.

18. The computer program product of claim 17, wherein the program instructions are further executable by the processor to cause the processor to:
parameterize, by the processor, using the machine learning model, the circuit model based on circuit data indicative of information for the circuit properties associated with one or more medical conditions.

19. The computer program product of claim 17, wherein the program instructions are further executable by the processor to cause the processor to:
provide, by the processor, the treatment data to an external system.

20. The computer program product of claim 17, wherein the different types of brain receptors comprise at least one of a cannabinoid receptor, a receptor associated with a norepinephrine transporter, a dopamine receptor, an inhibitory receptor, a nicotinic receptor, or a receptor associated with beta-amyloid plaque.

* * * * *